(12) United States Patent
Serhan et al.

(10) Patent No.: US 9,902,681 B2
(45) Date of Patent: Feb. 27, 2018

(54) N-3 IMMUNORESOLVENTS: STRUCTURES AND ACTIONS

(71) Applicant: THE BRIGHAM AND WOMEN'S HOSPITAL, INC., Boston, MA (US)

(72) Inventors: Charles N. Serhan, Needham, MA (US); Jesmond Dalli, London (GB)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/894,921

(22) PCT Filed: May 14, 2014

(86) PCT No.: PCT/US2014/037969
§ 371 (c)(1),
(2) Date: Nov. 30, 2015

(87) PCT Pub. No.: WO2014/193652
PCT Pub. Date: Dec. 4, 2014

(65) Prior Publication Data
US 2016/0115112 A1    Apr. 28, 2016

Related U.S. Application Data

(60) Provisional application No. 61/829,064, filed on May 30, 2013.

(51) Int. Cl.
*A61K 31/202* (2006.01)
*C07C 57/03* (2006.01)
*C07D 303/38* (2006.01)

(52) U.S. Cl.
CPC .......... *C07C 57/03* (2013.01); *C07D 303/38* (2013.01)

(58) Field of Classification Search
USPC ........................ 514/549, 560, 475
See application file for complete search history.

(56) References Cited

U.S. PATENT DOCUMENTS

| | | | |
|---|---|---|---|
| 2008/0161274 A1 | 7/2008 | Gjorstrup et al. | |
| 2009/0118243 A1 | 5/2009 | Gjorstrup | |
| 2011/0178047 A1* | 7/2011 | Arterburn | C07C 59/42 514/163 |
| 2012/0059061 A1* | 3/2012 | Arita | C07C 59/42 514/560 |

FOREIGN PATENT DOCUMENTS

| | | |
|---|---|---|
| JP | 2011-190184 A | 9/2011 |
| WO | 2006055965 A2 | 5/2006 |
| WO | 2008103753 A2 | 8/2008 |
| WO | WO 2012/135032 A2 | 10/2012 |
| WO | 2013170006 A2 | 11/2013 |

OTHER PUBLICATIONS

Bannenberg et al., "Molecular circuits of resolution: formation and actions of resolvins and protectins," J Immunol 2005, 174(7): 4345-4355.
Barrett et al., "Bifidobacterium breve with alpha-Linolenic Acid and Linoleic Acid Alters Fatty Acid Metabolism in the Maternal Separation Model of Irritable Bowel Syndrome," PLoS One 2012, 7(11): e48159.
Berge et al., "Pharmaceutical Salts," J. Pharm. Sci., 1977; 66:1; 19 pages.
Buckley et al., "The resolution of inflammation," Nat Rev Immunol 2013, 13(1): 59-66.
Calder, "Fatty acids and inflammation: the cutting edge between food and pharma," Eur J Pharmacol 2011, 668 Suppl 1: S50-58.
Chiang et al., "Infection regulates pro-resolving mediators that lower antibiotic requirements," Nature 2012, 484(7395): 524-528.
Chiu et al., "Omega-6 docosapentaenoic acid-derived resolvins and 17-hydroxydocosahexaenoic acid modulate macrophage function and alleviate experimental colitis," Inflamm Res 2012, 61(9): 967-976.
Colgan et al., "Contributions of neutrophils to resolution of mucosal inflammation," Immunol Res 2013, 55(1-3): 75-82.
Crawford et al, "A quantum theory for the irreplaceable role of docosahexaenoic acid in neural cell signalling throughout evolution," Prostaglandins Leukot Essent Fatty Acids 2013, 88(1): 5-13.
Dalli et al., "Novel n-3 Immunoresolvents: Structures and Actions," Scientific Reports 3(1940): 1-13, Jun. 2013. [retrieved from the Internet on Jan. 27, 2016). <URL: http://www.researchgate.net/publication/237056925_Novel_n-3_1mmunoresolvents_Structures_and_Actions>.
Dalli et al., "Specific lipid mediator signatures of human phagocytes: microparticles stimulate macrophage efferocytosis and pro-resolving mediators," Blood 2012, 120(15): e60-72.
Dangi et al., "Metabolism and biological production of resolvins derived from docosapentaenoic acid (DPAn-6)," Biochem Pharmacol 2010, 79(2): 251-260.
De Caterina, "n-3 fatty acids in cardiovascular disease," N Engl J Med 2011, 364(25): 2439-2450.
Flower et al., "Inhibition of prostaglandin biosynthesis," Biochem Pharmacol 1974, 23(10): 1439-1450.

(Continued)

*Primary Examiner* — Pancham Bakshi
(74) *Attorney, Agent, or Firm* — Quarles & Bardy LLP

(57) ABSTRACT

The invention describes novel mono-hydroxy, di-hydroxy and tri-hydroxy docosapentaenoic acid (DPA) analogs, their preparation, isolation, identification, purification and uses thereof. Resolution of inflammation is now held to be an active process where autacoids promote homeostasis. Using functional-metabololipidomics and in vivo systems, endogenous n-3 docosapentaenoic (DPA) acid is converted during inflammation-resolution in mice and by human leukocytes to novel n-3 products congenerous to D-series resolvins (Rv), protectins (PD) and maresins (MaR), termed specialized pro-resolving mediators (SPM). The new n-3 DPA structures include 7,8,17-trihydroxy-9,11,13,15E, 19Zdocosapentaenoic acid (RvD1n_3 DPA), 7, 14-dihydroxy-8, 10, 12, 16Z, 19Z-docosapentaenoic acid (MaR1n_3 DPA) and related bioactive products.

2 Claims, 14 Drawing Sheets

(56) References Cited

OTHER PUBLICATIONS

Furman et al., "Twenty-two year (1975 to 1997) trends in the incidence, in-hospital and long-term case fatality rates from initial Q-wave and non-Q-wave myocardial infarction: a multi-hospital, community-wide perspective," J Am Coll Cardiol 2001, 37(6): 1571-1580.

Giera et al., "Lipid and lipid mediator profiling of human synovial fluid in rheumatoid arthritis patients by means of LC-MS/MS," Biochim Biophys Acta 2012, 1821(11): 1415-1424.

Granger et al., "The microcirculation and inflammation: modulation of leukocyte-endothelial cell adhesion," J Leukoc Biol 1994, 55(5): 662-675.

Hussein et al., "Artificial rearing of infant mice leads to n-3 fatty acid deficiency in cardiac, neural and peripheral tissues," Lipids 2009, 44(8): 685-702.

Kasuga et al., "Rapid appearance of resolvin precursors in inflammatory exudates: novel mechanisms in resolution," J Immunol 2008, 181(12): 8677-8687.

Khaw et al., "Plasma phospholipid fatty acid concentration and incident coronary heart disease in men and women: the EPIC-Norfolk prospective study," PLoS Afed 2012, 9(7): e1001255.

Lemaitre et al., "Genetic loci associated with plasma phospholipid n-3 fatty acids: a meta-analysis of genome-wide association studies from the CHARGE Consortium," PLoS Genet 2011, 7(7): e1002193.

Luscinskas et al., "Cytokine-activated human endothelial monolayers support enhanced neutrophil transmigration via a mechanism involving both endothelialleukocyte adhesion molecule-1 and intercellular adhesion molecule-1" J Immunol 1991, 146(5): 1617-1625.

Mas et al., "Resolvins D1, D2, and Other Mediators of Self-Limited Resolution of Inflammation in Human Blood following n-3 Fatty Acid Supplementation," Clin Chem 2012, 58(10): 1476-1484.

Oda et al., "A case-control pilot study on n-3 polyunsaturated fatty acid as a negative risk factor for myocardial infarction," Int Heart J 2005, 46(4): 583-591.

Qiu et al., "IMP and AMP deaminase in reperfusion injury down-regulates neutrophil recruitment," Proc Natl Acad Sci U S A 2000, 97(8): 4267-4272.

Rapoport, "Translational studies on regulation of brain docosahexaenoic acid (DHA) metabolism in vivo," Prostaglandins Leukot Essent Fatty Acids 2013, 88(1): 79-85.

Rissanen et al., "Fish oil-derived fatty acids, docosahexaenoic acid and docosapentaenoic acid, and the risk of acute coronary events: the Kuopio ischaemic heart disease risk factor study," Circulation 2000, 102(22): 2677-2679.

Samuelsson, "Role of basic science in the development of new medicines: examples from the eicosanoid field," J Biol Chem 2012, 287(13): 10070-10080.

Serhan, "A search for endogenous mechanisms of anti-inflammation uncovers novel chemical mediators: missing links to resolution," Histochem Cell Biol 2004, 122(4): 305-321.

Serhan et al., "Macrophage proresolving mediator maresin 1 stimulates tissue regeneration and controls pain," FASEB J 2012, 26(4): 1755-1765.

Serhan et al., "Maresins: novel macrophage mediators with potent antiinflammatory and proresolving actions," J Exp Med 2009, 206(1): 15-23.

Serhan et al., "Novel functional sets of lipid-derived mediators with antiinflammatory actions generated from omega-3 fatty acids via cyclooxygenase 2-nonsteroidal antiinflammatory drugs and transcellular processing," J Exp Med 2000, 192(8): 1197-1204.

Serhan et al., "Resolution of inflammation: the beginning programs the end," Nat Immunol 2005, 6(12): 1191-1197.

Serhan et al., "Resolvins: a family of bioactive products of omega-3 fatty acid transformation circuits initiated by aspirin treatment that counter proinflammation signals," J Exp Med 2002, 196(8): 1025-1037.

Serhan et al., "Resolvins and protectins in inflammation resolution," Chem Rev 2011, 111(10): 5922-5943.

Shimizu, "Lipid mediators in health and disease: enzymes and receptors as therapeutic targets for the regulation of immunity and inflammation," Annu Rev Pharmacol Toxicol 2009, 49: 123-150.

Spite et al., "Novel lipid mediators promote resolution of acute inflammation: impact of aspirin and statins," Circ Res 2010, 107(10): 1170-1184.

Spite et al., "Resolvin D2 is a potent regulator of leukocytes and controls microbial sepsis," Nature 2009, 461(7268): 1287-1291.

Sun et al., "Blood concentrations of individual long-chain n-3 fatty acids and risk of nonfatal myocardial infarction," Am J Clin Nutr 2008, 88(1): 216-223.

Tabas et al., "Anti-inflammatory therapy in chronic disease: challenges and opportunities," Science 2013, 339(6116): 166-172.

van Gils et al., "Molecular and functional interactions among monocytes, platelets, and endothelial cells and their relevance for cardiovascular diseases," J Leukoc Biol 2009, 85(2): 195-204.

Yang et al., "Metabolomics-lipidomics of eicosanoids and docosanoids generated by phagocytes," Curr Protoc Immunol 2011, Chapter 14: Unit 14.26.

Zhang et al., "Resolvins: anti-inflammatory and proresolving mediators derived from omega-3 polyunsaturated fatty acids. Annu Rev Nutr 2012, 32: 203-227."

Supplementary European Search Report for Application No. 148051253, dated Dec. 12, 2016, 9 pages.

* cited by examiner

N-3 IMMUNORESOLVENTS: STRUCTURES AND ACTIONS

CROSS REFERENCE TO RELATED APPLICATIONS

The present application is a National Phase entry of PCT Application No. PCT/US2014/037969, filed May 14, 2014, which claims priority to U.S. Provisional Patent Application No. 61/829,064, filed May 30, 2013, the disclosures of which are incorporated by reference in their entireties.

STATEMENT REGARDING FEDERALLY SPONSORED RESEARCH

This invention was made with government support under grant P01GM095467 awarded by (the National Institutes of Health). The government has certain rights in the invention.

FIELD OF THE INVENTION

The invention relates generally to novel monohydroxy, dihydroxy and trihydroxy analogues of docosapentaenoic (DPA) all having a hydroxyl group at one or more of the 7, 14 and/or 17 positions of the 22 carbon chain.

BACKGROUND OF THE INVENTION

The resolution of acute inflammation is an active process temporally orchestrated by local-acting mediators that limit further neutrophil recruitment to sites of inflammation[1, 2, 3, 4]. During the onset of inflammation, chemical mediators, including the arachidonic acid-derived eicosanoids (e.g. leukotriene (LT) $B_4$ and prostaglandin (PG) $E_2$), mount initiation and propagation of inflammation[5, 6], actions that are actively counter-regulated and orchestrated by pro-resolution agonists[1, 2, 4]. These pro-resolving autacoids also stimulate the clearance of debris, apoptotic cells and bacteria, promoting homeostasis[1, 2, 7].

One of the key steps during resolution of inflammation is an increase in local vascular permeability leading to edema[6, 8] and the transport of n-3 essential fatty acids (EFA) from blood to the site of inflammation[9]. n-3 EFA are linked with protective actions in a number of inflammatory conditions including rheumatoid arthritis[10], neurological disorders[11] and cardiovascular disease[12]. At the site of inflammation, n-3 EFA are converted to novel potent mediators by exudate leukocytes that promote inflammation-resolution[1, 2, 13].

The E-series resolvins, e.g. resolvin (Rv) E1, are produced from 5Z,8Z,11Z,14Z,17Z-eicosapentaenoic acid (EPA)[14]. The D-series resolvins, which include Resolvin D1 (7S,8R,17S-trihydroxy-4Z,9E,11E,13Z,15E,19Z-docosahexaenoic acid; RvD1) and Resolvin D2 (7S,16R,17S-trihydroxy-4Z,8E,10Z,12E,14E,19Z-docosahexaenoic acid; RvD2), the protectins[15] and maresins[16] are biosynthesized from 4Z,7Z,10Z,13Z,16Z,19Z-docosahexaenoic acid (DHA). These potent autacoids were initially identified using temporal lipidomics with self-resolving exudates[14, 15] and are now appreciated for their ability to stereo-selectively promote inflammation-resolution by tempering leukocyte responses[16, 17, 13]. The resolvins, protectins and maresins are coined specialized pro-resolving mediators (SPM) that by definition limit further neutrophil recruitment to the site of inflammation and promote macrophage clearance of debris, apoptotic cells and bacteria[1, 2, 7]. In addition, the SPM exert potent actions in promoting wound repair and tissue regeneration as well as dampening inflammatory pain[16, 18]. Targeted lipid mediator metabololipidomics of tissues obtained from a number of species ranging from primordial organisms such as planaria[16] to humans[19, 20] indicates that SPM production, including RvD1, RvE1[19, 20] and maresin 1,[2, 14] is evolutionarily conserved.

In mammals, alpha-linolenic acid (9Z,12Z,15Z-octadecatrienoic acid; ALA) is converted via elongation and desaturation to EPA and subsequently to DHA. An intermediate in the conversion of EPA to DHA is n-3 docosapentaenoic acid (7Z,10Z,13Z,16Z,19Z-docosapentaenoic acid; n-3 DPA) 10, 12, 21. n-3 DPA carries 22 carbons and contains five double bonds, with the first double bond being found on carbon 7. The structural differences of n-3 DPA from EPA, DHA and n-6 docosapentaenoic acid (4Z,7Z,10Z,13Z,16Z,-docosapentaenoic acid; n-6 DPA), a biochemically distinct form of DPA where the first double bond is found on carbon 4, are thought to confer unique biophysical properties that are of functional relevance, for example in neuronal systems[22]. In humans, genome-wide association studies demonstrate that elevation in circulating levels of n-3 DPA and a concomitant decrease in DHA levels are associated with single nucleotide polymorphisms in the gene encoding for the fatty acid elongase 2 (ELOVL2)[21]. n-3 DPA is present in a number of mammalian tissues including plasma, brain, retina and heart at levels comparable to those of EPA and DHA[23]. Since circulating levels of n-3 DPA in human cohorts of European, African, Hispanic and Chinese ancestry with mutations in the ELOVL2 gene are elevated[21], it remained to be determined whether n-3 DPA is a precursor to novel bioactive molecules.

Therefore, a need exists for a further understanding of, an exploration and/or an identification of new useful materials previously not appreciated as potent biological mediators of interest.

BRIEF SUMMARY OF THE INVENTION

Resolution of inflammation is now held to be an active process where autacoids promote homeostasis. Using functional-metabololipidomics and in vivo systems, endogenous n-3 docosapentaenoic (DPA) acid is converted during inflammation-resolution in mice and by human leukocytes to novel n-3 products congenerous to D-series resolvins (Rv), protectins (PD) and maresins (MaR), termed specialized pro-resolving mediators (SPM). The new n-3 DPA structures include 7,8,17-trihydroxy-9,11,13,15E,19Z-docosapentaenoic acid (RvD1$_{n-3\ DPA}$), 7,14-dihydroxy-8,10,12,16Z,19Z-docosapentaenoic acid (MaR1$_{n-3\ DPA}$) and related bioactive products. Each n-3 DPA-SPM displayed protective actions from second organ injury and reduced systemic inflammation in ischemia-reperfusion. The n-3 DPA-SPM, including RvD1$_{n-3DPA}$ and MaR1$_{n-3DPA}$, each exerted potent leukocyte directed actions in vivo. With human leukocytes each n-3 DPA-SPM reduced neutrophil chemotaxis, adhesion and enhanced macrophage phagocytosis. Together, these findings demonstrate that n-3 DPA is converted to novel immunoresolvents with actions comparable to resolvins and are likely produced in humans when n-3 DPA is elevated.

The present invention surprisingly provides novel compounds, compositions and methods of use of novel epoxy, monohydroxy, dihydroxy and trihydroxy analogues of docosapentaenoic (DPA) all having a hydroxyl group at one or more of the 7, 14 and/or 17 positions of the 22 carbon chain. These materials are biogenically derived and/or isolated from inflammatory exudates.

In one embodiment, the invention pertains to a new and useful DPA analogue such as a compound comprising the formula (I):

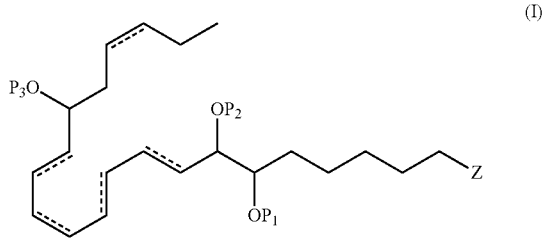

(I)

wherein each of $P_1$, $P_2$ and $P_3$ individually is a protecting group or a hydrogen atom;

wherein ----- is a double bond;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof, provided when Z is —C(O)OR$^d$, then R$^d$ for Z is not a hydrogen when $P_1$, $P_2$ and $P_3$ are all hydrogen atoms. In one aspect, $P_1$, $P_2$ and $P_3$ are all hydrogen atoms. In another aspect, the double bond at the 15 position is E. In still another aspect, the double bond at the 19 position is Z. In yet another aspect, the double bond at the 15 position is E and the double bond position at the 19 position is Z.

In one embodiment, one or more of $P_1$, $P_2$ and $P_3$ are hydrogen atoms and the double bond at the 15 position is E.

In another embodiment, one or more of $P_1$, $P_2$ and $P_3$ are hydrogen atoms and the double bond at the 19 position is Z.

In still another embodiment, one or more of $P_1$, $P_2$ and $P_3$ are hydrogen atoms, the double bond at the 15 position is E and the double bond at the 19 position is Z.

In still yet another embodiment, all $P_1$, $P_2$ and $P_3$ are hydrogen atoms, the double bond at the 15 position is E and the double bond at the 19 position is Z.

A particular isomer of interest of the DPA analogue (I) is (Ia) comprising the formula:

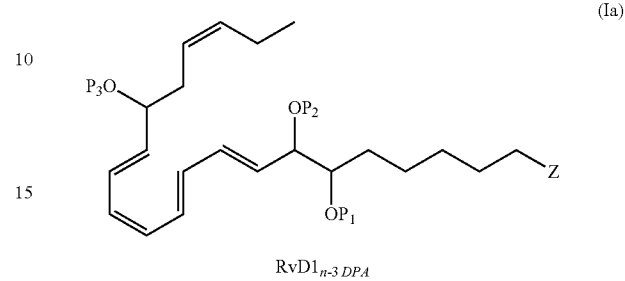

(Ia)

RvD1$_{n-3 DPA}$ wherein $P_1$, $P_2$, $P_3$, Z, R$^a$, R$^b$, R$^c$, R$^d$ and n are as previously defined.

In another aspect, the present invention provides new and useful DPA analogues such as purified compounds comprising the formulae (I) or (Ia):

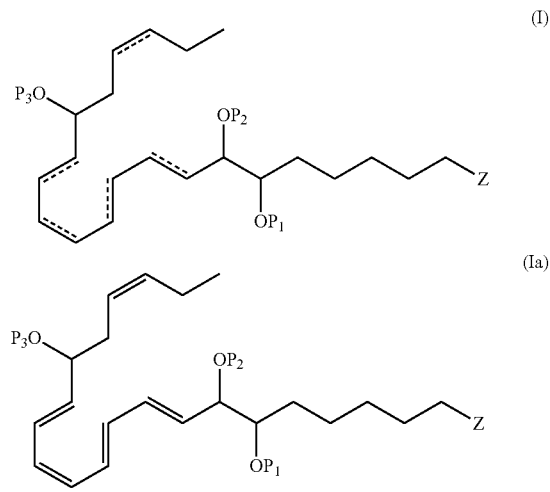

wherein $P_1$, $P_2$, -----, Z, R$^a$, R$^b$, R$^c$, R$^d$ and n are as previously defined. In one aspect, $P_1$, $P_2$ and $P_3$ are all hydrogen atoms. In one aspect, Z is —C(O)OR$^d$ and R$^d$ of Z is a hydrogen atom. In another embodiment, $P_1$, $P_2$ and $P_3$ are all hydrogen atoms, Z is —C(O)OR$^d$ and R$^d$ of Z is a hydrogen atom.

In one aspect, the double bond at the 15 position is E. In still another aspect, the double bond at the 19 position is Z. In yet another aspect, the double bond at the 15 position is E and the double bond position at the 19 position is Z.

In one embodiment, one or more of $P_1$, $P_2$ and $P_3$ are hydrogen atoms and the double bond at the 15 position is E.

In another embodiment, one or more of $P_1$, $P_2$ and $P_3$ are hydrogen atoms and the double bond at the 19 position is Z.

In still another embodiment, one or more of $P_1$, $P_2$ and $P_3$ are hydrogen atoms, the double bond at the 15 position is E and the double bond at the 19 position is Z.

In still yet another embodiment, each $P_1$, $P_2$ and $P_3$ is a hydrogen atom, the double bond at the 15 position is E and the double bond at the 19 position is Z.

In all of the above embodiments, in a particular aspect, Z is —C(O)OR$^d$ and R$^d$ of Z is a hydrogen atom.

It should be understood that compounds (I) and (Ia) include all pharmaceutically acceptable salts, esters thereof, the purified/isolated forms, as well as compounds wherein one or both of the possible hydroxyl groups are converted into a protecting group as described herein.

In another aspect, the invention pertains to a new and useful DPA analogue such as a compound comprising the formula (II):

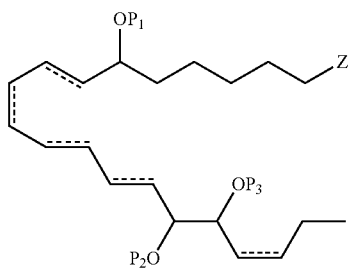

(II)

wherein P$_1$, P$_2$ P$_3$, ======, Z, R$^a$, R$^b$, R$^c$, R$^d$ and n are as previously defined, or a pharmaceutically acceptable salt thereof, provided when Z is —C(O)OR$^d$, then R$^d$ for Z is not a hydrogen when P$_1$, P$_2$ and P$_3$ are all hydrogen atoms.

In one embodiment, P$_1$, P$_2$ and P$_3$ are all hydrogen atoms.

In one aspect, the double bond at the 14 position is E. In another aspect, the double bond at the 19 position is Z. In yet another aspect, the double bond at the 14 position is E and the double bond at the 19 position is Z.

In one embodiment, one or more of P$_1$, P$_2$ and P$_3$ are hydrogen atoms and the double bond at the 14 position is E.

In another embodiment, one or more of P$_1$, P$_2$ and P$_3$ are hydrogen atoms and the double bond at the 19 position is Z.

In still another embodiment, one or more of P$_1$, P$_2$ and P$_3$ are hydrogen atoms, the double bond at the 14 position is E and the double bond at the 19 position is Z.

In still yet another embodiment, each P$_1$, P$_2$ and P$_3$ is a hydrogen atom, the double bond at the 14 position is E and the double bond at the 19 position is Z.

A particular isomer of interest of the DPA analogue (II) is (IIa) comprising the formula:

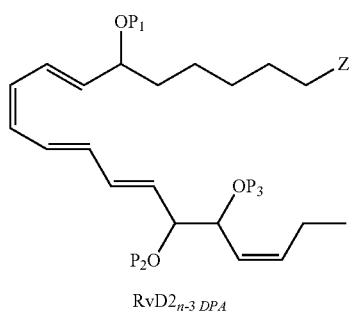

(IIa)

RvD2$_{n-3\ DPA}$ wherein P$_1$, P$_2$, P$_3$, Z, R$^a$, R$^b$, R$^c$, R$^d$ and n are as previously defined.

In another aspect, the present invention provides new and useful DPA analogues such as purified compounds comprising the formulae (II) or (IIa):

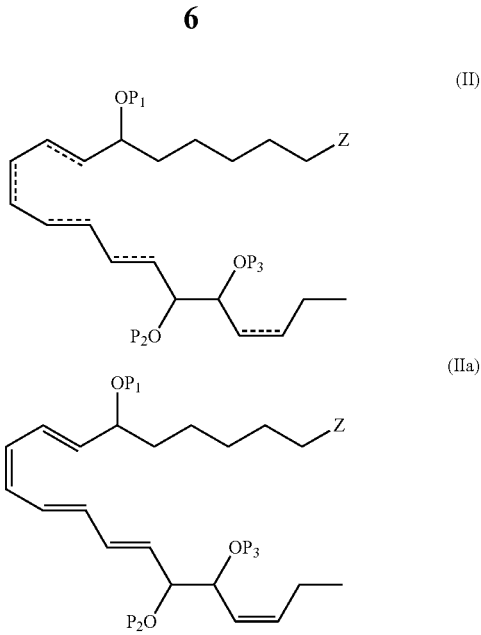

wherein P$_1$, P$_2$, P$_3$, ======, Z, R$^a$, R$^b$, R$^c$, R$^d$ and n are as previously defined. In one aspect, P$_1$, P$_2$ and P$_3$ are all hydrogen atoms. In one aspect, Z is —C(O)OR$^d$ and R$^d$ of Z is a hydrogen atom. In another embodiment, P$_1$, P$_2$ and P$_3$ are all hydrogen atoms, Z is —C(O)OR$^d$ and R$^d$ of Z is a hydrogen atom.

In one aspect, the double bond at the 14 position is E. In another aspect, the double bond at the 19 position is Z. In yet another aspect, the double bond at the 14 position is E and the double bond at the 19 position is Z.

In one embodiment, one or more of P$_1$, P$_2$ and P$_3$ are hydrogen atoms and the double bond at the 14 position is E.

In another embodiment, one or more of P$_1$, P$_2$ and P$_3$ are hydrogen atoms and the double bond at the 19 position is Z.

In still another embodiment, one or more of P$_1$, P$_2$ and P$_3$ are hydrogen atoms, the double bond at the 14 position is E and the double bond at the 19 position is Z.

In still yet another embodiment, each of P$_1$, P$_2$ and P$_3$ are hydrogen atoms, the double bond at the 14 position is E and the double bond at the 19 position is Z.

In all of the above embodiments, in a particular aspect, Z is —C(O)OR$^d$ and R$^d$ of Z is a hydrogen atom.

It should be understood that compounds (II) and (IIa) include all pharmaceutically acceptable salts, esters thereof, the purified/isolated forms, as well as compounds wherein one or both of the possible hydroxyl groups are converted into a protecting group as described herein.

In another aspect, the present invention provides new and useful DPA analogues such as a compound comprising formula (III):

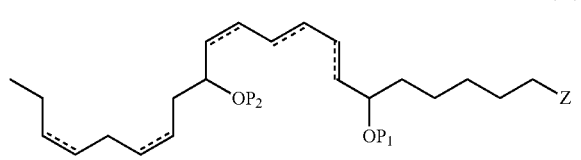

(III)

wherein P$_1$, P$_2$, ======, Z, R$^a$, R$^b$, R$^c$, R$^d$ and n are as previously defined, or a pharmaceutically acceptable salt thereof, provided when Z is —C(O)OR$^d$, then R$^d$ for Z is not a hydrogen when P$_1$ and P$_2$ are both hydrogen atoms.

In one embodiment, P$_1$ and P$_1$ are both hydrogen atoms.

In one aspect, the double bond at the 16 position is Z. In another aspect, the double bond at the 19 position is Z. In still another aspect, the double bond at the 16 position is Z and the double bond at the 19 position is Z.

In one embodiment, one or more of P$_1$ and P$_2$ are hydrogen atoms and the double bond at the 16 position is Z.

In another embodiment, one or more of P$_1$ and P$_2$ are hydrogen atoms and the double bond at the 19 position is Z.

In still another embodiment, one or more of P$_1$ and P$_2$ are hydrogen atoms, the double bond at the 16 position is Z and the double bond at the 19 position is Z.

In yet another embodiment, both P$_1$ and P$_2$ are hydrogen atoms, the double bond at the 16 position is Z and the double bon at the 19 position is Z.

A particular isomer of interest of the DPA analogue (III) is (IIIa) comprising the formula:

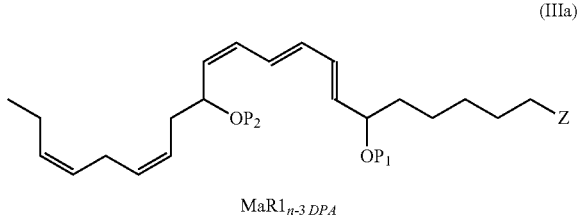

MaR1$_{n-3\,DPA}$ wherein P$_1$, P$_2$, Z, R$^a$, R$^b$, R$^c$, R$^d$ and n are as previously defined. In another aspect, the present invention provides new and useful DPA analogues such as purified compounds comprising the formulae (III) or (IIIa):

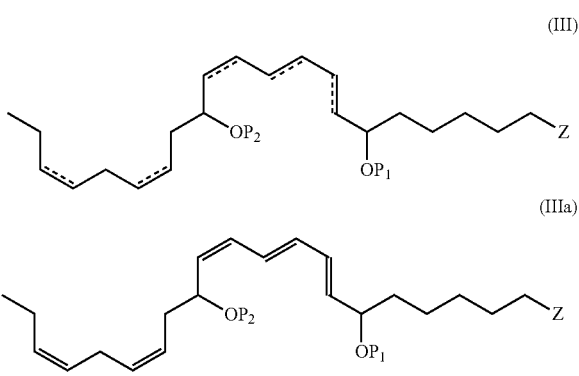

wherein P$_1$, P$_2$, $=====$, Z, R$^a$, R$^b$, R$^c$, R$^d$ and n are as previously defined. In one aspect, P$_1$ and P$_2$ are both hydrogen atoms. In one aspect, Z is —C(O)OR$^d$ and R$^d$ of Z is a hydrogen atom. In another embodiment, P$_1$ and P$_2$ are both hydrogen atoms, Z is —C(O)OR$^d$ and R$^d$ of Z is a hydrogen atom.

In one aspect, the double bond at the 16 position is Z. In another aspect, the double bond at the 19 position is Z. In still another aspect, the double bond at the 16 position is Z and the double bond at the 19 position is Z.

In one embodiment, one or more of P$_1$ and P$_2$ are hydrogen atoms and the double bond at the 16 position is Z.

In another embodiment, one or more of P$_1$ and P$_2$ are hydrogen atoms and the double bond at the 19 position is Z.

In still another embodiment, one or more of P$_1$ and P$_2$ are hydrogen atoms, the double bond at the 16 position is Z and the double bond at the 19 position is Z.

In yet another embodiment, both P$_1$ and P$_2$ are hydrogen atoms, the double bond at the 16 position is Z and the double bond at the 19 position is Z.

In all of the above embodiments, in a particular aspect, Z is —C(O)OR$^d$ and R$^d$ of Z is a hydrogen atom.

It should be understood that compounds (III) and (IIIa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (IV):

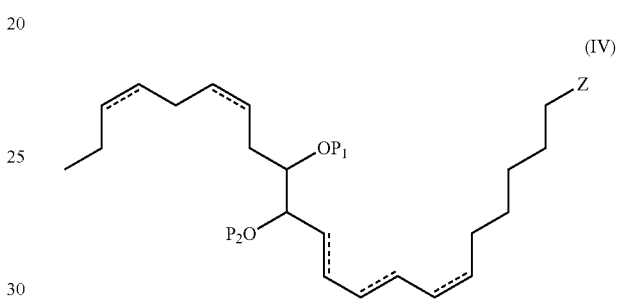

wherein P$_1$, P$_2$, $=====$, Z, R$^a$, R$^b$, R$^c$, R$^d$ and n are as previously defined, or a pharmaceutically acceptable salt thereof, provided when Z is —C(O)OR$^d$, then R$^d$ for Z is not a hydrogen when P$_1$ and P$_2$ are both hydrogen atoms.

In one embodiment, P$_1$ and P$_1$ are both hydrogen atoms.

In one aspect, the double bond at the 7 position is Z. In another aspect, the double bond at the 16 position is Z. In yet another aspect, the double bond at the 19 position is Z. In still other aspects, the double bond at the 7 position is Z, the double bond at the 16 position is Z, the double bond at the 19 position is Z and combinations thereof, e.g., both 7 and 16 are Z. In still yet another embodiment, the double bonds at the 7, 16 and 19 positions are all the Z configuration.

In one embodiment, one or more of P$_1$ and P$_1$ are hydrogen atoms and the double bond at the 7 position is Z.

In another embodiment, one or more of P$_1$ and P$_1$ are hydrogen atoms and the double bond at the 16 position is Z.

In still another embodiment, one or more of P$_1$ and P$_1$ are hydrogen atoms and the double bond at the 19 position is Z.

In still yet another embodiment, one or more of P$_1$ and P$_1$ are hydrogen atoms and at least two of the double bonds at the 7, 16 and/or 19 positions are Z.

In yet another embodiment, both P$_1$ and P$_1$ are hydrogen atoms and at least two of the double bonds at the 7, 16 and/or 19 positions are Z.

In still another embodiment, both P$_1$ and P$_1$ are hydrogen atoms and two of the double bonds at the 7, 16 and 19 positions are Z.

A particular isomer of interest of the DPA analogue (IV) is (IVa) comprising the formula:

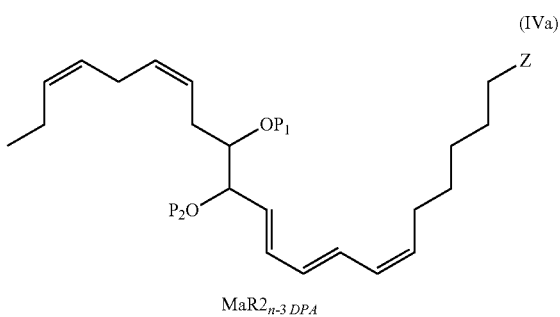

MaR2$_{n-3\,DPA}$ wherein $P_1$, $P_2$, Z, $R^a$, $R^b$, $R^c$, $R^d$ and n are as previously defined. In another aspect, the present invention provides new and useful DPA analogues such as purified compounds comprising the formulae (IV) or (IVa):

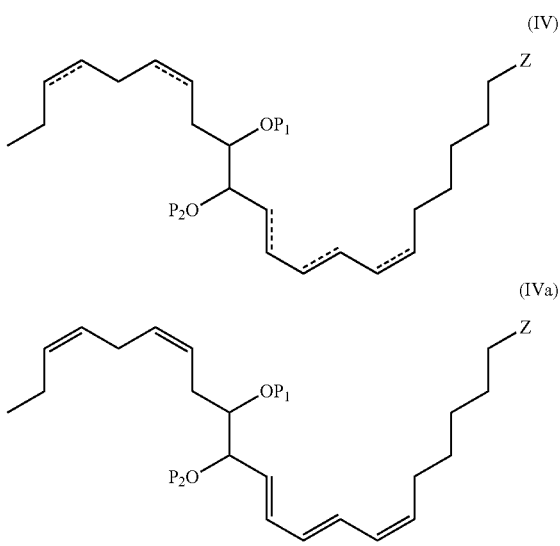

wherein $P_1$, $P_2$, =====, Z, $R^a$, $R^b$, $R^c$, $R^d$ and n are as previously defined. In one aspect, $P_1$ and $P_2$ are both hydrogen atoms. In one aspect, Z is —C(O)OR$^d$ and R$^d$ of Z is a hydrogen atom. In another embodiment, $P_1$ and $P_2$ are both hydrogen atoms, Z is —C(O)OR$^d$ and R$^d$ of Z is a hydrogen atom.

In one aspect, the double bond at the 7 position is Z. In another aspect, the double bond at the 16 position is Z. In yet another aspect, the double bond at the 19 position is Z. In still other aspects, the double bond at the 7 position is Z, the double bond at the 16 position is Z, the double bond at the 19 position is Z and combinations thereof, e.g., both 7 and 16 are Z. In still yet another embodiment, the double bonds at the 7, 16 and 19 positions are all the Z configuration.

In one embodiment, one or more of $P_1$ and $P_1$ are hydrogen atoms and the double bond at the 7 position is Z.

In another embodiment, one or more of $P_1$ and $P_1$ are hydrogen atoms and the double bond at the 16 position is Z.

In still another embodiment, one or more of $P_1$ and $P_1$ are hydrogen atoms and the double bond at the 19 position is Z.

In still yet another embodiment, one or more of $P_1$ and $P_1$ are hydrogen atoms and at least two of the double bonds at the 7, 16 and/or 19 positions are Z.

In yet another embodiment, both $P_1$ and $P_1$ are hydrogen atoms and at least two of the double bonds at the 7, 16 and/or 19 positions are Z.

In still another embodiment, both $P_1$ and $P_1$ are hydrogen atoms and two of the double bonds at the 7, 16 and 19 positions are Z.

In all of the above embodiments, in a particular aspect, Z is —C(O)OR$^d$ and R$^d$ of Z is a hydrogen atom.

It should be understood that compounds (IV) and (IVa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (V):

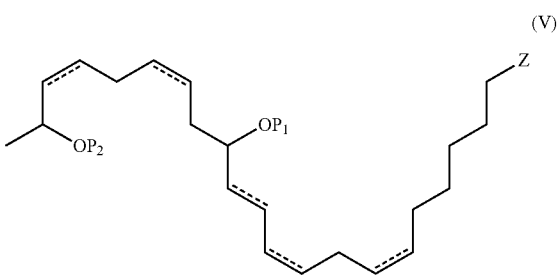

wherein $P_1$, $P_2$, =====, Z, $R^a$, $R^b$, $R^c$, $R^d$ and n are as previously defined, or a pharmaceutically acceptable salt thereof, provided when Z is —C(O)OR$^d$, then R$^d$ for Z is not a hydrogen when $P_1$ and $P_2$ are both hydrogen atoms. In one embodiment, $P_1$ and $P_1$ are both hydrogen atoms.

In one aspect, one or more of the double bonds at the 7, 10, 16 and/or 19 positions are of the Z configuration. For example, in one embodiment, the 7, 16 and 19 double bonds are Z. Another example is where the double bonds at the 10, 16 and 19 positions are all Z.

In another aspect, the double bonds at the 7, 10, 16 and 19 positions are all Z.

In still another aspect, the double bond at the 12 position is the E configuration. Therefore, embodiments include compounds wherein one or more of the double bonds at the 7, 10, 16 and/or 19 positions are of the Z configuration where the double bond at the 12 position is E.

Embodiments also include compounds wherein all the double bonds at the 7, 10, 16 and 19 positions are of the Z configuration where the double bond at the 12 position is E.

Embodiments further include compounds wherein one or more of $P_1$ and $P_1$ are hydrogen atoms and wherein one or more of the double bonds at the 7, 10, 16 and/or 19 positions are of the Z configuration where the double bond at the 12 position is E.

Additional embodiments include compounds wherein one or more of $P_1$ and $P_1$ are hydrogen atoms and wherein the double bonds at the 7, 10, 16 and 19 positions are of the Z configuration where the double bond at the 12 position is E.

Embodiments further include compounds wherein $P_1$ and $P_2$ are both hydrogen atoms and wherein one or more of the double bonds at the 7, 10, 16 and/or 19 positions are of the Z configuration where the double bond at the 12 position is E.

Additional embodiments include compounds wherein $P_1$ and $P_2$ are both hydrogen atoms and wherein the double bonds at the 7, 10, 16 and 19 positions are of the Z configuration where the double bond at the 12 position is E.

A particular isomer of interest of the DPA analogue (V) is (Va) comprising the formula:

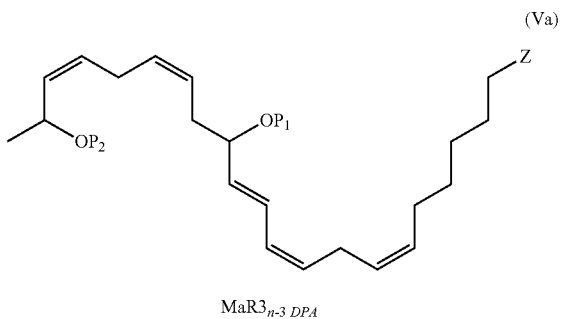

MaR3$_{n-3\ DPA}$ wherein $P_1$, $P_2$, Z, $R^a$, $R^b$, $R^c$, $R^d$ and n are as previously defined.

In another aspect, the present invention provides new and useful DPA analogues such as purified compounds comprising the formulae (V) or (Va):

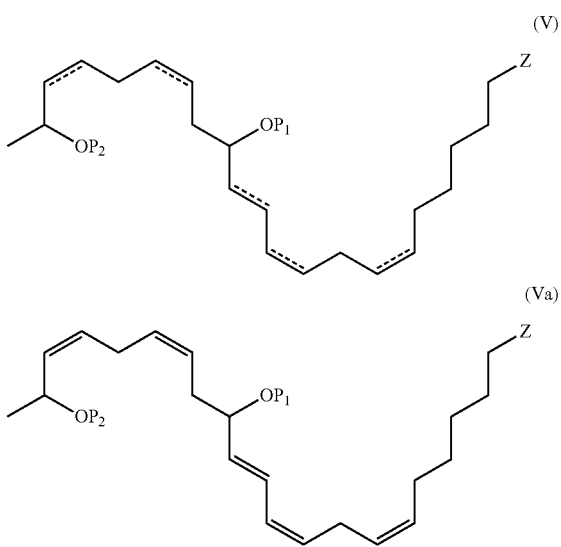

wherein $P_1$, $P_2$, =====, Z, $R^a$, $R^b$, $R^c$, $R^d$ and n are as previously defined. In one aspect, $P_1$ and $P_2$ are both hydrogen atoms. In one aspect, Z is —C(O)OR$^d$ and R$^d$ of Z is a hydrogen atom. In another embodiment, $P_1$ and $P_2$ are both hydrogen atoms, Z is —C(O)OR$^d$ and R$^d$ of Z is a hydrogen atom.

In one aspect, one or more of the double bonds at the 7, 10, 16 and/or 19 positions are of the Z configuration. For example, in one embodiment, the 7, 16 and 19 double bonds are Z. Another example is where the double bonds at the 10, 16 and 19 positions are all Z.

In another aspect, the double bonds at the 7, 10, 16 and 19 positions are all Z.

In still another aspect, the double bond at the 12 position is the E configuration. Therefore, embodiments include compounds wherein one or more of the double bonds at the 7, 10, 16 and/or 19 positions are of the Z configuration where the double bond at the 12 position is E.

Embodiments also include compounds wherein all the double bonds at the 7, 10, 16 and 19 positions are of the Z configuration where the double bond at the 12 position is E.

Embodiments further include compounds wherein one or more of $P_1$ and $P_1$ are hydrogen atoms and wherein one or more of the double bonds at the 7, 10, 16 and/or 19 positions are of the Z configuration where the double bond at the 12 position is E.

Additional embodiments include compounds wherein one or more of $P_1$ and $P_1$ are hydrogen atoms and wherein the double bonds at the 7, 10, 16 and 19 positions are of the Z configuration where the double bond at the 12 position is E.

Embodiments further include compounds wherein $P_1$ and $P_2$ are both hydrogen atoms and wherein one or more of the double bonds at the 7, 10, 16 and/or 19 positions are of the Z configuration where the double bond at the 12 position is E.

Additional embodiments include compounds wherein $P_1$ and $P_2$ are both hydrogen atoms and wherein the double bonds at the 7, 10, 16 and 19 positions are of the Z configuration where the double bond at the 12 position is E.

In all of the above embodiments, in a particular aspect, Z is —C(O)OR$^d$ and R$^d$ of Z is a hydrogen atom.

It should be understood that compounds (V) and (Va) include all pharmaceutically acceptable salts, esters thereof, the purified/isolated forms, as well as compounds wherein one or both of the possible hydroxyl groups are converted into a protecting group as described herein.

It should be understood that where a double bond is designated as a specific carbon position, e.g., the 7 position, that the double bond is formed with the next higher carbon number, for example, carbon position 8. This is based on convention in the art.

Other useful DPA derived analogues include:

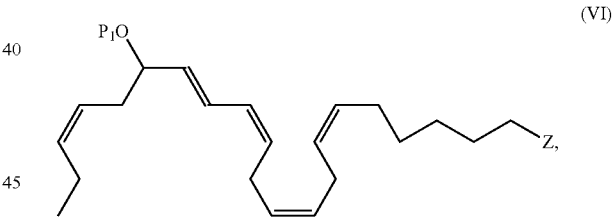

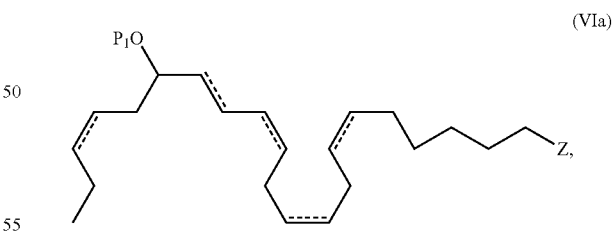

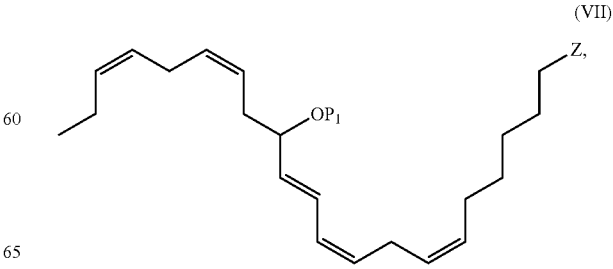

-continued
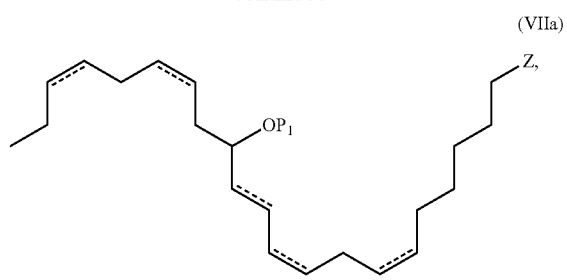
(VIIa)
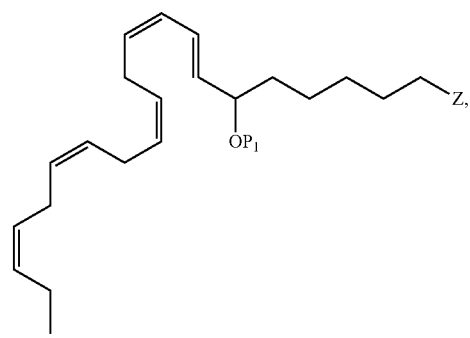
(VIII)
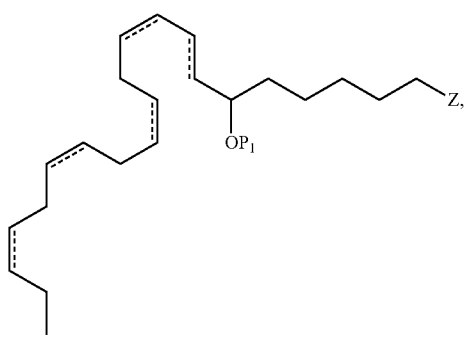
(VIIIa)
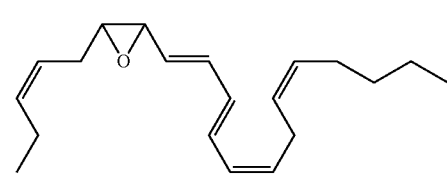
(IX)
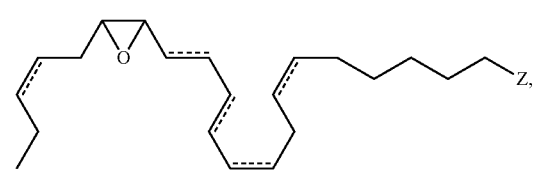
(IXa)
-continued
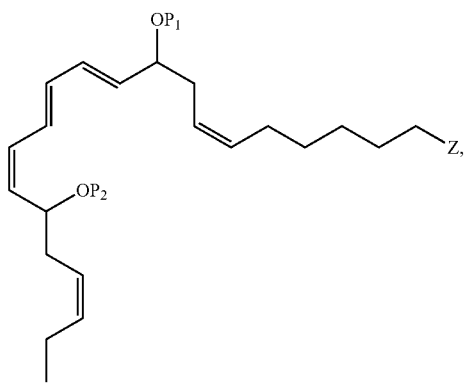
(X)
PD1$_{n\text{-}3\,DPA}$
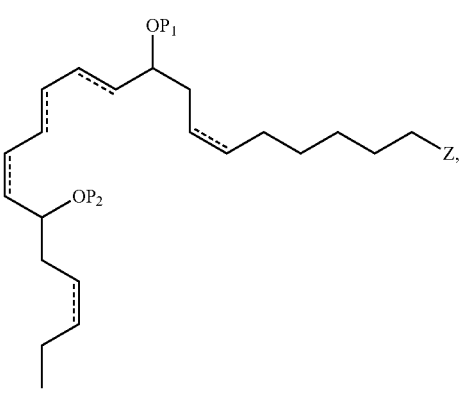
(Xa)
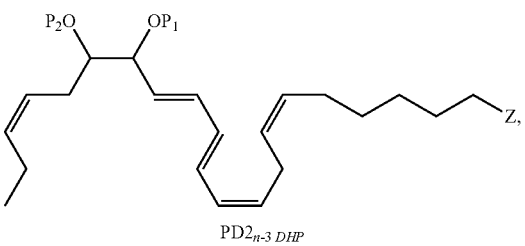
(XI)
PD2$_{n\text{-}3\,DHP}$
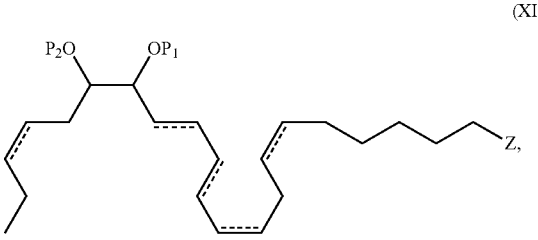
(XIa)
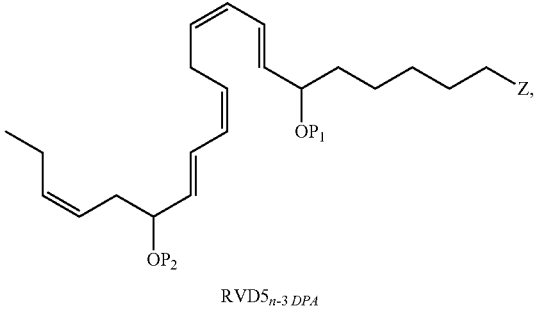
(XII)
RVD5$_{n\text{-}3\,DPA}$ -continued (XIIa)

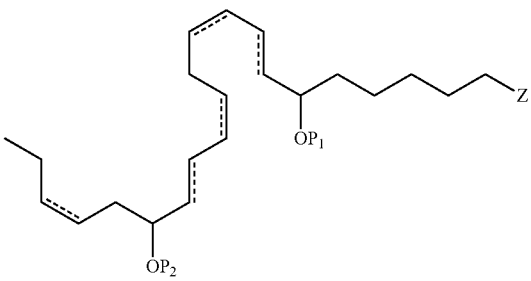

wherein $P_1$, $P_2$, =====, Z, $R^a$, $R^b$, $R^c$, $R^d$ and n are as previously defined, or a pharmaceutically acceptable salt thereof, provided when Z is —C(O)OR$^d$, then $R^d$ for Z is not a hydrogen when $P_1$ and $P_2$ are both hydrogen atoms. In one embodiment, $P_1$ and $P_1$ are both hydrogen atoms.

In other embodiments when compounds VIa through XIIa are purified, then $P_1$ and/or $P_2$ are both hydrogen atoms. In one aspect, Z is —C(O)OR$^d$ and $R^d$ of Z is a hydrogen atom. In another embodiment, $P_1$ and/or $P_2$ are both hydrogen atoms, Z is —C(O)OR$^d$ and $R^d$ of Z is a hydrogen atom.

It should be understood that compounds (VI) through (XIIa) include all pharmaceutically acceptable salts, esters thereof, the purified/isolated forms, as well as compounds wherein one or both of the possible hydroxyl groups are converted into a protecting group as described herein.

It should also be understood that any of the compounds described herein can be used for treatment or prevention of any of the ailments, diseases, or afflictions noted throughout the specification.

In another aspect, the present invention provides pharmaceutical compositions comprising one or more compounds of the invention, with or without other active pharmaceutical ingredients, in admixture with a pharmaceutically acceptable vehicle. Such a preparation can be administered according to the methods of the current invention.

In yet another aspect, the present invention is drawn to methods for treating or preventing inflammation or inflammatory disease in a mammal. The method involves administering a prophylactically or therapeutically effective amount of at least one compound of the invention, or a pharmaceutical composition thereof. For example, the compounds of the invention can be used to treat or prevent inflammation, cancer, neurodegeneration, memory loss, wrinkles, psoriasis, dandruff or dermatitis by administering to an individual in need thereof, an effective amount of any of the compounds described herein.

Additionally, the compounds of the invention can be used to neural development, fetal development, homeostasis, tissue remodeling, or wound repair by administering to an individual in need thereof, an effective amount of any of the compounds described herein.

Additional features and advantages of the invention will become more apparent from the following detailed description and claims.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
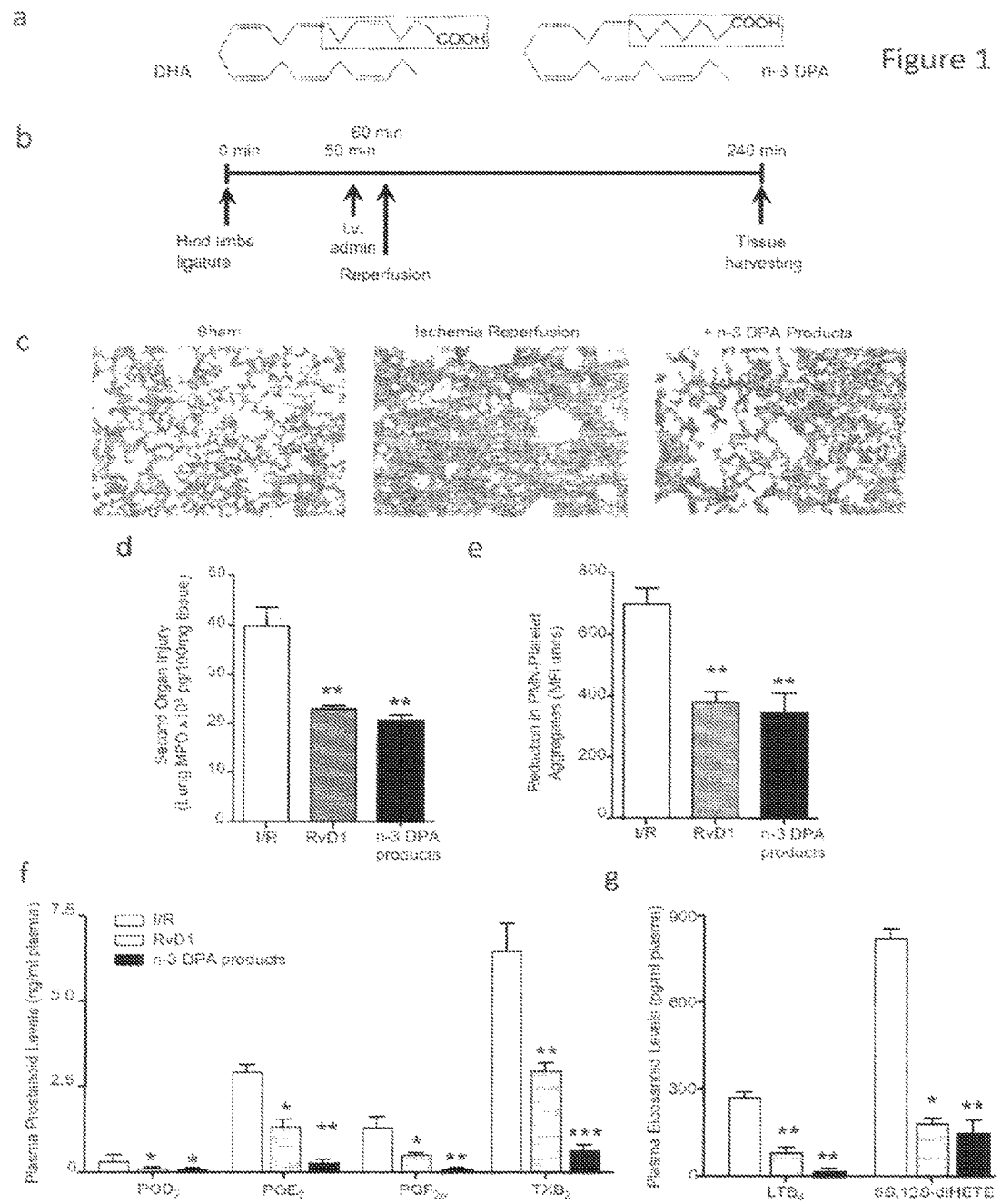
FIG. 1. n-3 DPA-derived products display potent anti-inflammatory and tissue protective actions in vivo that are comparable to RvD1. (a) Structures of DHA and n-3 DPA. (b) Ischemia was induced by applying tourniquets to the hind limb of 6-8-week-old male FvB mice. After 1 h, tourniquets were removed and reperfusion ensued for 3 h. 10 min prior to reperfusion, vehicle (saline containing 0.1% EtOH), RvD1 (500 ng) or a mixture of n-3 DPA-derived products (see Methods for details) were administered intravenously. At the end of reperfusion, lungs were collected; (c) tissue histology by H&E staining (×200) and (d) MPO levels were assessed. (e) Blood was collected, incubated with rat anti-mouse Ly6G and rat anti-mouse CD41 antibodies and neutrophil leukocyte aggregates were assessed by flow cytometry. (f) Plasma prostanoid and (g) leukotriene levels were assessed by lipid mediator metabololipidomics. Results are mean±SEM. n=4 mice per group. (*P<0.05; vs. vehicle group). Results c are representative n=4. Results d-e are mean±SEM. n=4. *P<0.05, **P<0.01 vs. vehicle mice.

In one embodiment, the invention pertains to a new and useful DPA analogue such as a compound comprising the formula (I):

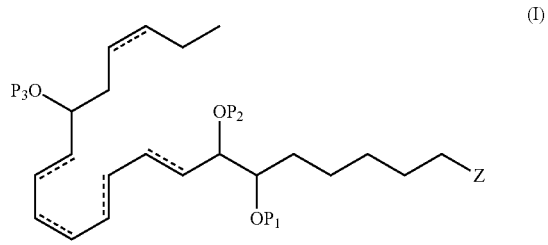

wherein each of $P_1$, $P_2$ and $P_3$ individually is a protecting group or a hydrogen atom;

wherein ------ is a double bond;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR'R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_2$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof, provided when Z is —C(O)OR$^d$, then R$^d$ for Z is not a hydrogen when $P_1$, $P_2$ and $P_3$ are all hydrogen atoms. In one aspect, $P_1$, $P_2$ and $P_3$ are all hydrogen atoms. In another aspect, the double bond at the 15 position is E and at the 19 position is Z.

A particular isomer of interest of the DPA analogue (I) is (Ia) comprising the formula:

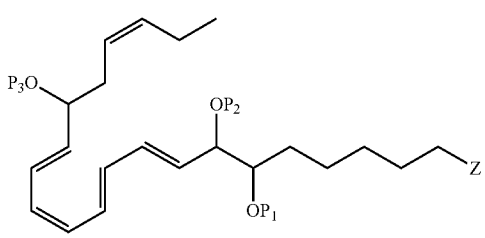

RvD1$_{n-3\ DPA}$ wherein $P_1$, $P_2$, $P_3$, Z, R$^a$, R$^b$, R$^c$, R$^d$ and n are as previously defined.

In another aspect, the present invention provides new and useful DPA analogues such as purified compounds comprising the formulae (I) or (Ia):

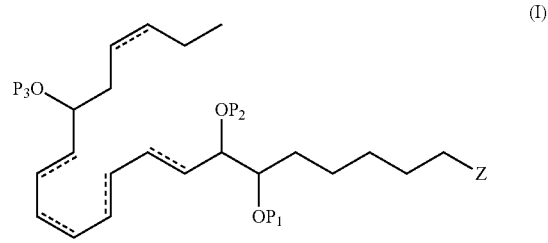

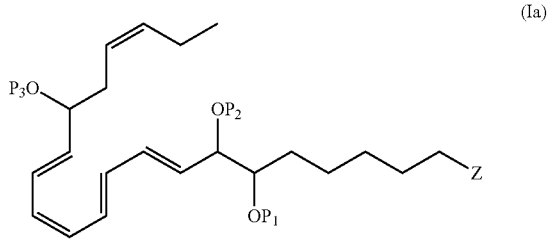

wherein $P_1$, $P_2$, ------, Z, R$^a$, R$^b$, R$^c$, R$^d$ and n are as previously defined. In one aspect, $P_1$, $P_2$ and $P_3$ are all hydrogen atoms. In one aspect, Z is —C(O)OR$^d$ and R$^d$ of Z is a hydrogen atom. In another embodiment, $P_1$, $P_2$ and $P_3$ are all hydrogen atoms, Z is —C(O)OR$^d$ and R$^d$ of Z is a hydrogen atom.

It should be understood that compounds (I) and (Ia) include all pharmaceutically acceptable salts, esters thereof, the purified/isolated forms, as well as compounds wherein one or both of the possible hydroxyl groups are converted into a protecting group as described herein.

In another aspect, the invention pertains to a new and useful DPA analogue such as a compound comprising the formula (II):

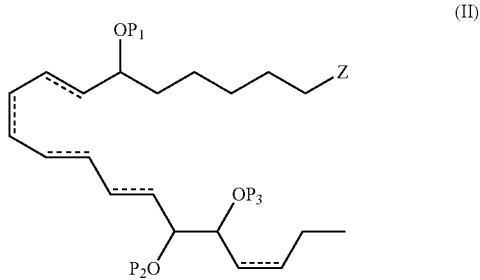

wherein $P_1$, $P_2$, $P_3$, ------, Z, R$^a$, R$^b$, R$^c$, R$^d$ and n are as previously defined, or a pharmaceutically acceptable salt thereof, provided when Z is —C(O)OR$^d$, then R$^d$ for Z is not a hydrogen when $P_1$, $P_2$ and $P_3$ are all hydrogen atoms.

In one embodiment, $P_1$, $P_2$ and $P_3$ are all hydrogen atoms. In another aspect, the double bond at the 14 position is E and at the 19 position is Z.

A particular isomer of interest of the DPA analogue (II) is (IIa) comprising the formula:

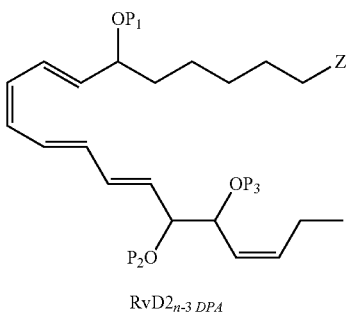

RvD2$_{n-3\,DPA}$ wherein $P_1$, $P_2$, $P_3$, Z, $R^a$, $R^b$, $R^c$, $R^d$ and n are as previously defined.

In another aspect, the present invention provides new and useful DPA analogues such as purified compounds comprising the formulae (II) or (IIa):

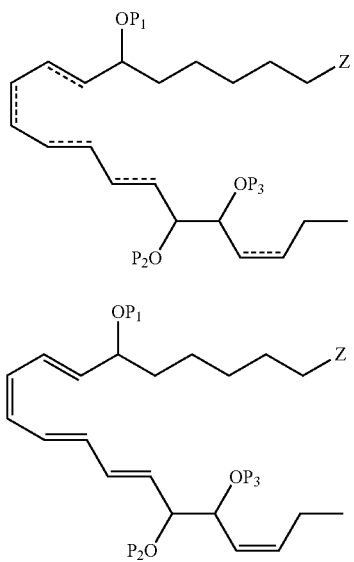

wherein $P_1$, $P_2$, $P_3$, -----, Z, $R^a$, $R^b$, $R^c$, $R^d$ and n are as previously defined. In one aspect, $P_1$, $P_2$ and $P_3$ are all hydrogen atoms. In one aspect, Z is —C(O)OR$^d$ and R$^d$ of Z is a hydrogen atom. In another embodiment, $P_1$, $P_2$ and $P_3$ are all hydrogen atoms, Z is —C(O)OR$^d$ and R$^d$ of Z is a hydrogen atom.

It should be understood that compounds (II) and (IIa) include all pharmaceutically acceptable salts, esters thereof, the purified/isolated forms, as well as compounds wherein one or both of the possible hydroxyl groups are converted into a protecting group as described herein.

In another aspect, the present invention provides new and useful DPA analogues such as a compound comprising formula (III):

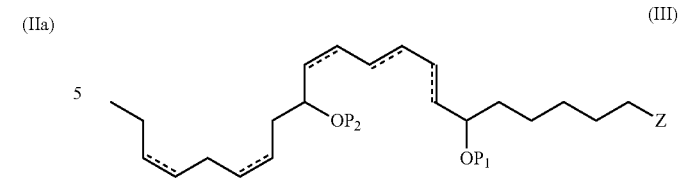

wherein $P_1$, $P_2$, -----, Z, $R^a$, $R^b$, $R^c$, $R^d$ and n are as previously defined, or a pharmaceutically acceptable salt thereof, provided when Z is —C(O)OR$^d$, then R$^d$ for Z is not a hydrogen when $P_1$ and $P_2$ are both hydrogen atoms.

In one embodiment, $P_1$ and $P_1$ are both hydrogen atoms. In another aspect, the double bond at the 16 position is Z and at the 19 position is Z.

A particular isomer of interest of the DPA analogue (III) is (IIIa) comprising the formula:

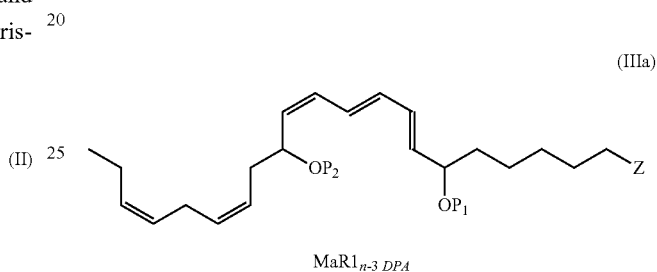

MaR1$_{n-3\,DPA}$ wherein $P_1$, $P_2$, Z, $R^a$, $R^b$, $R^c$, $R^d$ and n are as previously defined.

In another aspect, the present invention provides new and useful DPA analogues such as purified compounds comprising the formulae (III) or (IIIa):

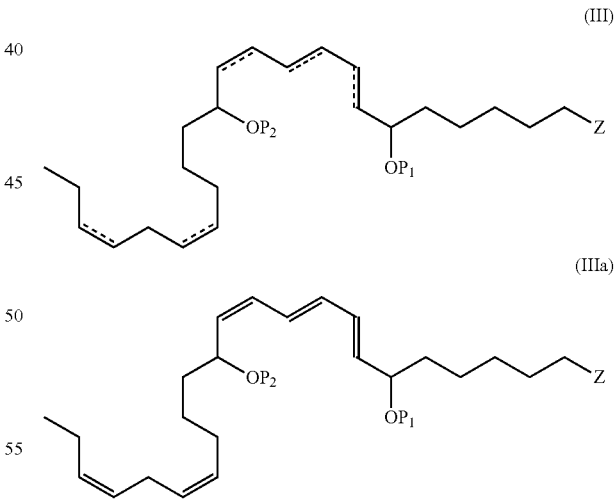

wherein $P_1$, $P_2$, -----, Z, $R^a$, $R^b$, $R^c$, $R^d$ and n are as previously defined. In one aspect, $P_1$ and $P_2$ are both hydrogen atoms. In one aspect, Z is —C(O)OR$^d$ and R$^d$ of Z is a hydrogen atom. In another embodiment, $P_1$ and $P_2$ are both hydrogen atoms, Z is —C(O)OR$^d$ and R$^d$ of Z is a hydrogen atom.

It should be understood that compounds (III) and (IIIa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (IV):

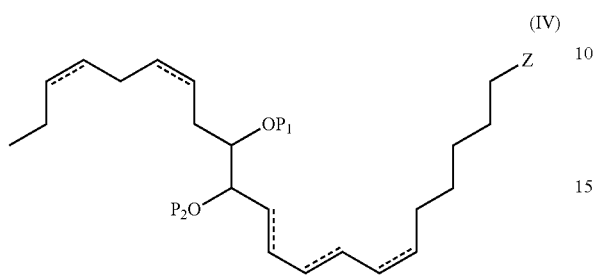

(IV)

wherein $P_1$, $P_2$, =====, Z, $R^a$, $R^b$, $R^c$, $R^d$ and n are as previously defined, or a pharmaceutically acceptable salt thereof, provided when Z is —C(O)OR$^d$, then $R^d$ for Z is not a hydrogen when $P_1$ and $P_2$ are both hydrogen atoms. In one embodiment, $P_1$ and $P_1$ are both hydrogen atoms. In another aspect, the double bond at the 7 position is Z, at the 16 position is Z and at the 19 position is Z.

A particular isomer of interest of the DPA analogue (IV) is (IVa) comprising the formula:

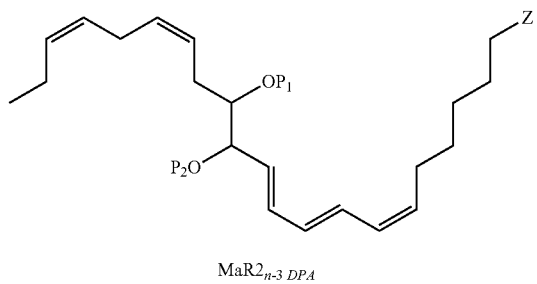

(IVa)

MaR2$_{n-3\ DPA}$ wherein $P_1$, $P_2$, Z, $R^a$, $R^b$, $R^c$, $R^d$ and n are as previously defined.

In another aspect, the present invention provides new and useful DPA analogues such as purified compounds comprising the formulae (IV) or (IVa):

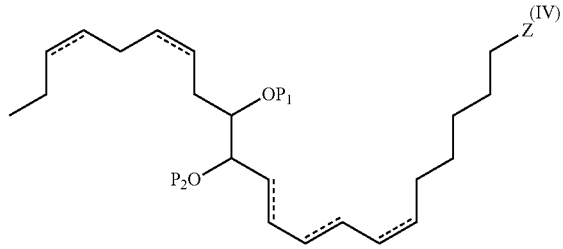

(IV)

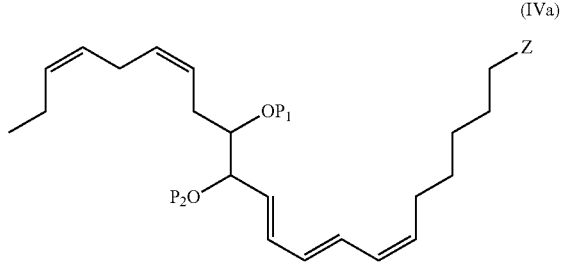

(IVa)

wherein $P_1$, $P_2$, =====, Z, $R^a$, $R^b$, $R^c$, $R^d$ and n are as previously defined. In one aspect, $P_1$ and $P_2$ are both hydrogen atoms. In one aspect, Z is —C(O)OR$^d$ and $R^d$ of Z is a hydrogen atom. In another embodiment, $P_1$ and $P_2$ are both hydrogen atoms, Z is —C(O)OR$^d$ and $R^d$ of Z is a hydrogen atom.

It should be understood that compounds (IV) and (IVa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (V):

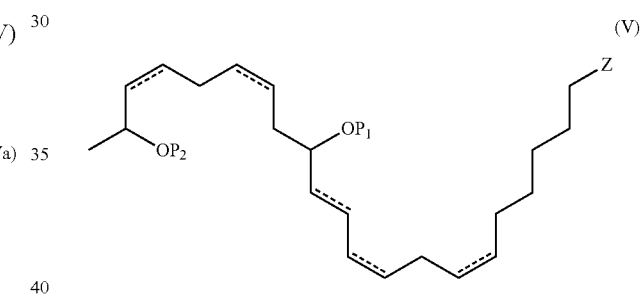

(V)

wherein $P_1$, $P_2$, =====, Z, $R^a$, $R^b$, $R^c$, $R^d$ and n are as previously defined, or a pharmaceutically acceptable salt thereof, provided when Z is —C(O)OR$^d$, then $R^d$ for Z is not a hydrogen when $P_1$ and $P_2$ are both hydrogen atoms. In one embodiment, $P_1$ and $P_1$ are both hydrogen atoms.

In one aspect, one or more of the double bonds at the 7, 10, 16 and/or 19 positions are of the Z configuration. For example, in one embodiment, the 7, 16 and 19 double bonds are Z. Another example is where the double bonds at the 10, 16 and 19 positions are all Z.

In another aspect, the double bonds at the 7, 10, 16 and 19 positions are all Z.

In still another aspect, the double bond at the 12 position is the E configuration. Therefore, embodiments include compounds wherein one or more of the double bonds at the 7, 10, 16 and/or 19 positions are of the Z configuration where the double bond at the 12 position is E.

Embodiments also include compounds wherein all the double bonds at the 7, 10, 16 and 19 positions are of the Z configuration where the double bond at the 12 position is E.

Embodiments further include compounds wherein $P_1$ and $P_2$ are both hydrogen atoms and wherein one or more of the double bonds at the 7, 10, 16 and/or 19 positions are of the Z configuration where the double bond at the 12 position is E.

Additional embodiments include compounds wherein $P_1$ and $P_2$ are both hydrogen atoms and wherein the double bonds at the 7, 10, 16 and 19 positions are of the Z configuration where the double bond at the 12 position is E.

A particular isomer of interest of the DPA analogue (V) is (Va) comprising the formula:

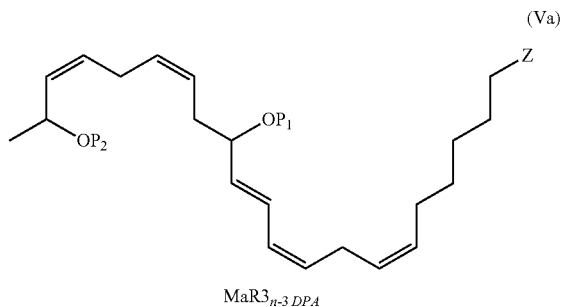

MaR3$_{n-3\,DPA}$ wherein $P_1$, $P_2$, Z, $R^a$, $R^b$, $R^c$, $R^d$ and n are as previously defined.

In another aspect, the present invention provides new and useful DPA analogues such as purified compounds comprising the formulae (V) or (Va):

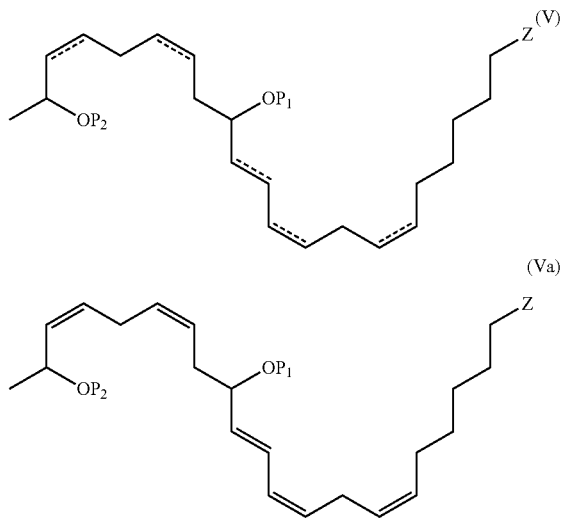

wherein $P_1$, $P_2$, $\mathrel{\overline{\overline{\phantom{===}}}}$, Z, $R^a$, $R^b$, $R^c$, $R^d$ and n are as previously defined. In one aspect, $P_1$ and $P_2$ are both hydrogen atoms. In one aspect, Z is —C(O)OR$^d$ and R$^d$ of Z is a hydrogen atom. In another embodiment, $P_1$ and $P_2$ are both hydrogen atoms, Z is —C(O)OR$^d$ and R$^d$ of Z is a hydrogen atom.

It should be understood that compounds (V) and (Va) include all pharmaceutically acceptable salts, esters thereof, the purified/isolated forms, as well as compounds wherein one or both of the possible hydroxyl groups are converted into a protecting group as described herein.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Compounds of the invention" refers to the di-hydroxy, trihydroxy, and/or epoxide DPA analogues and compounds encompassed by generic formulae disclosed herein and includes any specific compounds within those formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention also include isotopically labeled compounds where one or more atoms have an atomic mass different from the atomic mass conventionally found in nature.

The compounds depicted throughout the specification contain ethylenically unsaturated sites. Where carbon carbon double bonds exist, the configurational chemistry can be either cis (Z) or trans (E) and the depictions throughout the specification are not meant to be limiting. The depictions are, in general, presented based upon the configurational chemistry of DPA compounds, and although not to be limited by theory, are believed to possess similar configuration chemistry. The use of $\mathrel{\overline{\overline{\phantom{===}}}}$ reflects this throughout the specification and claims so that both cis (Z) and trans (E) isomers are contemplated. In certain embodiments the configuration of the ethylenic bond is known and is particularly described.

In one aspect of the invention, the compound(s) of the invention are substantially purified and/or isolated by techniques known in the art. The purity of the purified compounds is generally at least about 90%, preferably at least about 95%, and most preferably at least about 99% by weight.

Thus, the term "purified" as used herein does not require absolute purity; rather, it is intended as a relative term. For example, a purified DPA analogue can be one in which the subject DPA analogue is at a higher concentration than the analogue would be in its natural environment within an organism. For example, a DPA analogue of the invention can be considered purified if the analogue content in the preparation represents at least 50%, 60%, 70%, 80%, 85%, 90%, 92%, 95%, 98%, or 99% of the total analogue content of the preparation.

"Biological activity" and its contextual equivalents "activity" and "bioactivity" means that a compound elicits a statistically valid effect in any one biological test assays. Preferably, the threshold for defining an "active" compound will be reproducible and statistically valid effects of at least 25% deviation from untreated control at concentrations at or lower than 1 μM.

"Biological test assay" means a specific experimental procedure. Non-limiting examples of biological test assays include: 1) ligand binding, either direct or indirect, to a purified target, subcellular fraction, intact cell, or cell or tissue extract; 2) metabolic protection with enhanced half-life when exposed to a purified target, subcellular fraction, intact cell, cell or tissue extract, or administered to intact organism by any route; 3) prevention, reversal, or amelioration of cell- and tissue-based functional responses recognized by skilled artisans to represent surrogates for anti-inflammatory action (e.g., altered cytokine production and release); and 4) prevention, reversal, or amelioration of symptoms and/or disease processes in animal models of inflammation and inflammatory disease.

"Detectable label" means any chemical or biological modality which can be used to track, trace, localize, quantify, immobilize, purify, or identify compounds through appropriate means of detection known in the art. Non-limiting examples of detectable labels include fluorescence, phosphorescence, luminescence, radioactive or biospecific affinity capture labels.

"Electronegative group" is a chemical group that tends to acquire rather than lose electrons in its chemical interactions. Examples of electronegative groups include, but are not limited to, —$NO_2$, ammonium salts, sulfonyl groups, carbonyl groups, halogens, esters, carboxylic acids, nitriles, etc.

"In Situ" refers to and includes the terms "in vivo," "ex vivo" and "in vitro" as these terms are commonly recognized and understood by the skilled artisan. Moreover, the phrase "in situ" is employed herein in its broadest connotative and denotative context to identify an entity, cell, or tissue as found or in place, without regard to its source or origin, its condition or status or its duration or longevity at that location or position.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) salts formed when an basic proton is present in the parent compound such as acid addition salts, formed with inorganic acids such as hydrochloric acid, hydrobromic acid, sulfuric acid, nitric acid, phosphoric acid, and the like; or those formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton is present in the parent compound and either is replaced by a metal ion, e.g., an alkali metal ion, an alkaline earth ion, or an aluminum ion; or coordinates with an organic base such as ethanolamine, diethanolamine, triethanolamine, N-methylglucamine, triethylamine, propylamino, diazabicycloundecane and the like.

"Pharmaceutically acceptable vehicle" refers to a diluent, adjuvant, excipient or carrier with which a compound of the invention is administered.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other nontoxic compatible substances employed in pharmaceutical formulations.

"Prodrug" refers to a derivative of a drug molecule that requires a transformation within the body to release the active drug. Prodrugs are frequently (though not necessarily) pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, imine, phosphonyl, phosphoryl or sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which contain different functional groups other than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2.sup.nd ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitroveratryloxycarbonyl ("NVOC") and the like. Representative hydroxy protecting groups include, but are not limited to, those where the hydroxy group is either acylated (e.g., methyl and ethyl esters, acetate or propionate groups or glycol esters) or alkylated such as benzyl, and trityl ethers as well as alkyl ethers, tetrahydropyranyl ethers, trialkylsilyl ethers (e.g., TMS or TIPPS groups) and allyl ethers.

"Subject" means living organisms susceptible to conditions or diseases caused or contributed to by inflammation, inflammatory responses, vasoconstriction and myeloid suppression. Examples of subjects include humans, dogs, cats, cows, goats and mice. The term subject is further intended to include transgenic species such as, for example, transgenic mice.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkdiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkdiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl-, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In a preferred embodiment, the alkdiyl group is (C1-C6) alkdiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra)

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

The present invention is also drawn to methods for treating arterial inflammation, arthritis, psoriasis, urticara, vasculitis, asthma, ocular inflammation, pulmonary inflammation, pulmonary fibrosis, seborrheic dermatitis, pustular dermatosis, or cardiovascular diseases in a subject by administration of one or more of the DPA analogs described herein. Disease states or conditions that are associated with inflammation such as the recruitment of neutrophils, leukocytes and/or cytokines are included within the general scope of inflammation and include, for example, Addiction, AIDS, Alcohol-related disorders, Allergy, Alzheimer's disease, Anesthesiology, Anti-infectives, Anti-inflammatory agents, Arthritis, Asthma, Atherosclerosis, Bone diseases, Breast cancer, Cancer, Cardiovascular diseases, Child health, Colon cancer, Congenital defects, Decision analysis, Degenerative neurologic disorders, Dementia, Dermatology, Diabetes mellitus, Diagnostics, Drug delivery, Drug discovery/screen, Endocrine disorders, ENT, Epidemiology, Eye diseases, Fetal and maternal medicine, Gastrointestinal disorders, Gene therapy, Genetic diagnostics, Genetics, Genitourinary disorders, Geriatric medicine, Growth and Development, Hearing, Hematologic disorders, Hepatobiliary disorders, Hypertension, Imaging, Immunology, Infectious diseases, Leukemia/lymphoma, Lung cancer, Metabolic disorders, Neonatology, Neurological disorders, Neuromuscular disorders, Nuclear medicine, Obesity/eating disorders, Orthopedic, Other, Parasitic diseases, Perinatal disorders, Pregnancy, Preventative medicine, Prostate cancer, Psychiatric disorders, Pulmonary disorders, Radiology, Renal disorders, Reproduction, Rheumatic diseases, Stroke, Surgical, Transplantation, Vaccines, Vascular medicine, Wound healing, oral infections, periodontal disease, brain injury, trauma and neuronal inflammation, and Women's health.

The pharmaceutical compositions of the invention include a "therapeutically effective amount" or a "prophylactically effective amount" of one or more of the DPA analogs of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the DPA analog may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the DPA analog and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a DPA analog of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one DPA analog, in combination with a pharmaceutically acceptable carrier.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1 19 which is incorporated herein by reference).

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The invention features an article of manufacture that contains packaging material and DPA analog formulation contained within the packaging material. This formulation contains an at least one DPA analog and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable DPA analogs are described herein.

The present invention surprisingly provides novel compounds, compositions and methods of use pertaining to monohydroxy, dihydroxy and/or trihydroxy analogues of new and useful DPA analogue such as a compound comprising the formula (I):

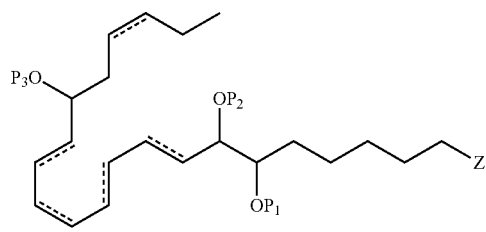

(I)

wherein each of $P_1$, $P_2$ and $P_3$ individually is a protecting group or a hydrogen atom;
wherein ===== is a double bond;
wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;
each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;
each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR'R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_2$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;
each n, independently is an integer from 0 to 3; and
each R$^d$, independently is a protecting group or R$^a$;
or a pharmaceutically acceptable salt thereof, provided when Z is —C(O)OR$^d$, then R$^d$ for Z is not a hydrogen when $P_1$, $P_2$ and $P_3$ are all hydrogen atoms. In one aspect, $P_1$, $P_2$ and $P_3$ are all hydrogen atoms. In another aspect, the double bond at the 15 position is E and at the 19 position is Z.

A particular isomer of interest of the DPA analogue (I) is (Ia) comprising the formula:

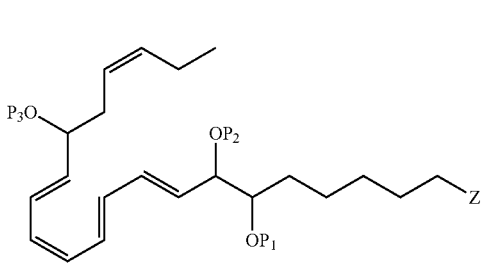

(Ia)

RvD1$_{n-3\ DPA}$ wherein $P_1$, $P_2$, $P_3$, Z, $R^a$, $R^b$, $R^c$, $R^d$ and n are as previously defined.

In another aspect, the present invention provides new and useful DPA analogues such as purified compounds comprising the formulae (I) or (Ia):

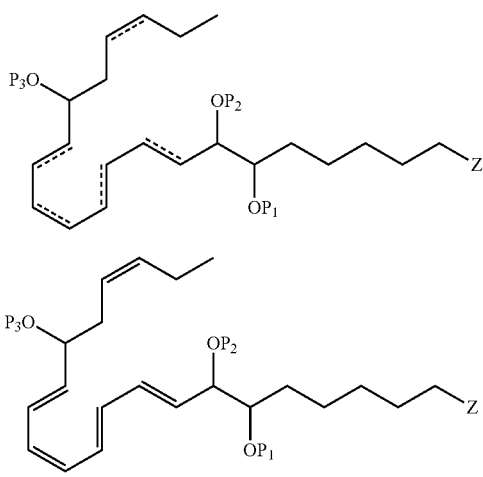

(I)

(Ia)

wherein $P_1$, $P_2$, ======, Z, $R^a$, $R^b$, $R^c$, $R^d$ and n are as previously defined. In one aspect, $P_1$, $P_2$ and $P_3$ are all hydrogen atoms. In one aspect, Z is —C(O)OR$^d$ and R$^d$ of Z is a hydrogen atom. In another embodiment, $P_1$, $P_2$ and $P_3$ are all hydrogen atoms, Z is —C(O)OR$^d$ and R$^d$ of Z is a hydrogen atom.

It should be understood that compounds (I) and (Ia) include all pharmaceutically acceptable salts, esters thereof, the purified/isolated forms, as well as compounds wherein one or both of the possible hydroxyl groups are converted into a protecting group as described herein.

In another aspect, the invention pertains to a new and useful DPA analogue such as a compound comprising the formula (II):

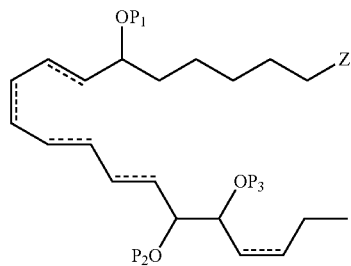

(II)

wherein $P_1$, $P_2$ $P_3$, ======, Z, $R^a$, $R^b$, $R^c$, $R^d$ and n are as previously defined, or a pharmaceutically acceptable salt thereof, provided when Z is —C(O)OR$^d$, then R$^d$ for Z is not a hydrogen when $P_1$, $P_2$ and $P_3$ are all hydrogen atoms.

In one embodiment, $P_1$, $P_2$ and $P_3$ are all hydrogen atoms. In another aspect, the double bond at the 14 position is E and at the 19 position is Z.

A particular isomer of interest of the DPA analogue (II) is (IIa) comprising the formula:

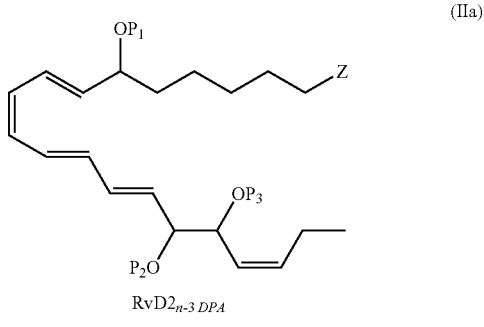

(IIa)

RvD2$_{n-3\,DPA}$ wherein $P_1$, $P_2$, $P_3$, Z, $R^a$, $R^b$, $R^c$, $R^d$ and n are as previously defined.

In another aspect, the present invention provides new and useful DPA analogues such as purified compounds comprising the formulae (II) or (IIa):

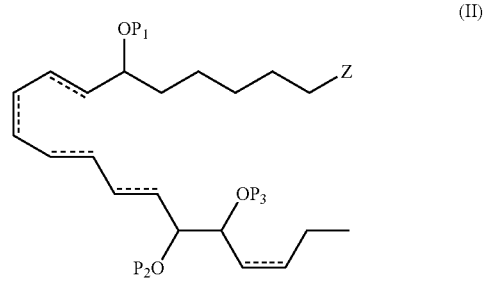

(II)

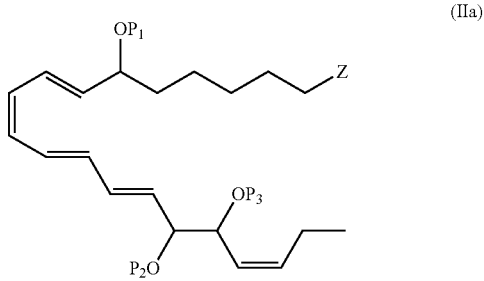

(IIa)

wherein $P_1$, $P_2$, $P_3$, ======, Z, $R^a$, $R^b$, $R^c$, $R^d$ and n are as previously defined. In one aspect, $P_1$, $P_2$ and $P_3$ are all hydrogen atoms. In one aspect, Z is —C(O)OR$^d$ and R$^d$ of Z is a hydrogen atom. In another embodiment, $P_1$, $P_2$ and $P_3$ are all hydrogen atoms, Z is —C(O)OR$^d$ and R$^d$ of Z is a hydrogen atom.

It should be understood that compounds (II) and (IIa) include all pharmaceutically acceptable salts, esters thereof, the purified/isolated forms, as well as compounds wherein one or both of the possible hydroxyl groups are converted into a protecting group as described herein.

In another aspect, the present invention provides new and useful DPA analogues such as a compound comprising formula (III):

(III)

wherein $P_1$, $P_2$, ======, Z, $R^a$, $R^b$, $R^c$, $R^d$ and n are as previously defined, or a pharmaceutically acceptable salt thereof, provided when Z is —C(O)OR$^d$, then $R^d$ for Z is not a hydrogen when $P_1$ and $P_2$ are both hydrogen atoms.

In one embodiment, $P_1$ and $P_1$ are both hydrogen atoms. In another aspect, the double bond at the 16 position is Z and at the 19 position is Z.

A particular isomer of interest of the DPA analogue (III) is (IIIa) comprising the formula:

(IIIa)

MaR1$_{n-3\,DPA}$ wherein $P_1$, $P_2$, Z, $R^a$, $R^b$, $R^c$, $R^d$ and n are as previously defined.

In another aspect, the present invention provides new and useful DPA analogues such as purified compounds comprising the formulae (III) or (IIIa):

(III)

(IIIa)

wherein $P_1$, $P_2$, ======, Z, $R^a$, $R^b$, $R^c$, $R^d$ and n are as previously defined. In one aspect, $P_1$ and $P_2$ are both hydrogen atoms. In one aspect, Z is —C(O)OR$^d$ and $R^d$ of Z is a hydrogen atom. In another embodiment, $P_1$ and $P_2$ are both hydrogen atoms, Z is —C(O)OR$^d$ and $R^d$ of Z is a hydrogen atom.

It should be understood that compounds (III) and (IIIa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (IV):

(IV)

wherein $P_1$, $P_2$, ======, Z, $R^a$, $R^b$, $R^c$, $R^d$ and n are as previously defined, or a pharmaceutically acceptable salt thereof, provided when Z is —C(O)OR$^d$, then $R^d$ for Z is not a hydrogen when $P_1$ and $P_2$ are both hydrogen atoms. In one embodiment, $P_1$ and $P_1$ are both hydrogen atoms. In another aspect, the double bond at the 7 position is Z, at the 16 position is Z and at the 19 position is Z.

A particular isomer of interest of the DPA analogue (IV) is (IVa) comprising the formula:

(IVa)

MaR2$_{n-3\,DPA}$ wherein $P_1$, $P_2$, Z, $R^a$, $R^b$, $R^c$, $R^d$ and n are as previously defined.

In another aspect, the present invention provides new and useful DPA analogues such as purified compounds comprising the formulae (IV) or (IVa):

(IV)

(IVa)

wherein $P_1$, $P_2$, ======, Z, $R^a$, $R^b$, $R^c$, $R^d$ and n are as previously defined. In one aspect, $P_1$ and $P_2$ are both hydrogen atoms. In one aspect, Z is —C(O)OR$^d$ and R$^d$ of Z is a hydrogen atom. In another embodiment, P$_1$ and P$_2$ are both hydrogen atoms, Z is —C(O)OR$^d$ and R$^d$ of Z is a hydrogen atom.

It should be understood that compounds (IV) and (IVa) include all pharmaceutically acceptable salts, esters thereof, the purified/isolated forms, as well as compounds wherein one or both of the possible hydroxyl groups are converted into a protecting group as described herein.

In yet another aspect, the present invention provides new and useful DPA analogues such as a compound comprising formula (V):

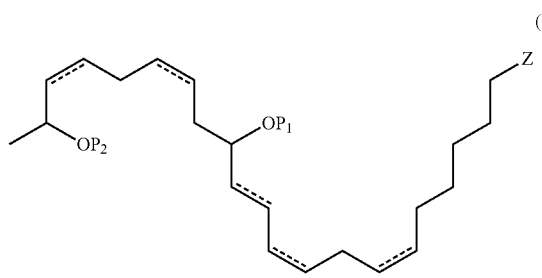

(V)

wherein P$_1$, P$_2$, ------, Z, R$^a$, R$^b$, R$^c$, R$^d$ and n are as previously defined, or a pharmaceutically acceptable salt thereof, provided when Z is —C(O)OR$^d$, then R$^d$ for Z is not a hydrogen when P$_1$ and P$_2$ are both hydrogen atoms. In one embodiment, P$_1$ and P$_1$ are both hydrogen atoms. In another aspect, the double bonds at the 7, 10, 12, 16 and 19 positions are all Z.

A particular isomer of interest of the DPA analogue (V) is (Va) comprising the formula:

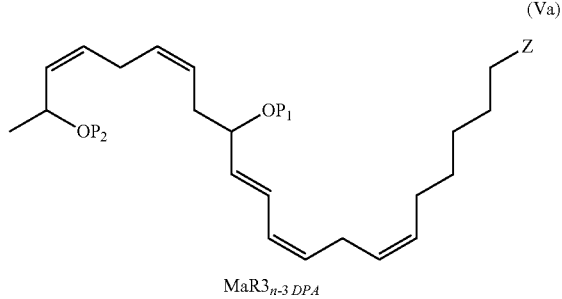

MaR3$_{n-3\,DPA}$ (Va)

wherein P$_1$, P$_2$, Z, R$^a$, R$^b$, R$^c$, R$^d$ and n are as previously defined.

In another aspect, the present invention provides new and useful DPA analogues such as purified compounds comprising the formulae (V) or (Va):

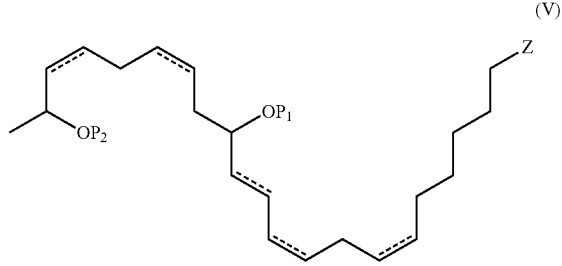

(V)

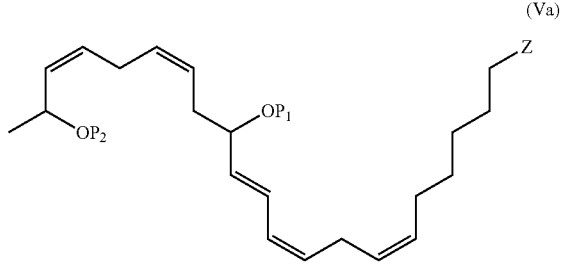

(Va)

wherein P$_1$, P$_2$, ------, Z, R$^a$, R$^b$, R$^c$, R$^d$ and n are as previously defined. In one aspect, P$_1$ and P$_2$ are both hydrogen atoms. In one aspect, Z is —C(O)OR$^d$ and R$^d$ of Z is a hydrogen atom. In another embodiment, P$_1$ and P$_2$ are both hydrogen atoms, Z is —C(O)OR$^d$ and R$^d$ of Z is a hydrogen atom.

It should be understood that compounds (V) and (Va) include all pharmaceutically acceptable salts, esters thereof, the purified/isolated forms, as well as compounds wherein one or both of the possible hydroxyl groups are converted into a protecting group as described herein.

Other useful DPA derived analogues include:

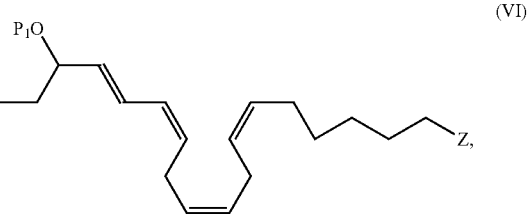

(VI)

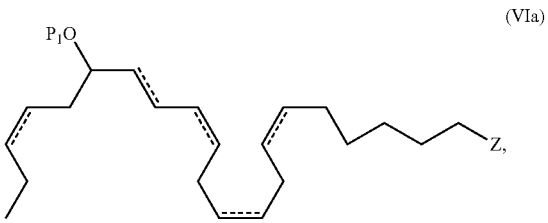

(VIa)

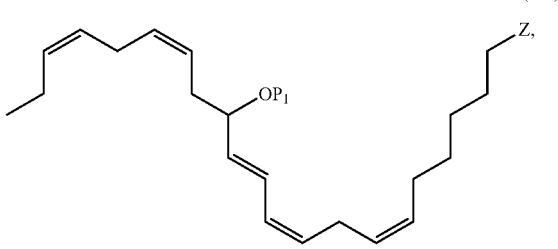

(VII)

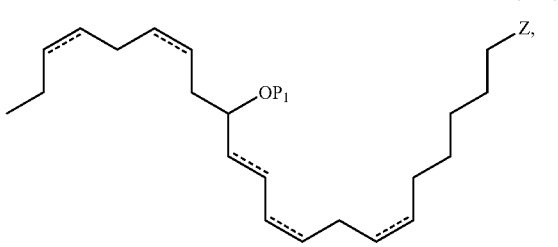

(VIIa)

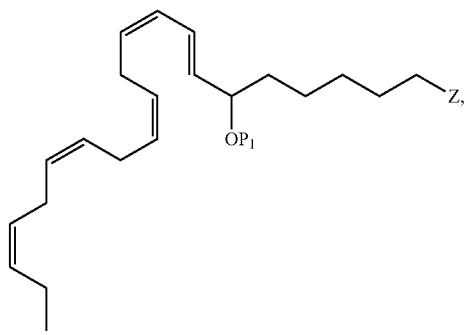
(VIII)
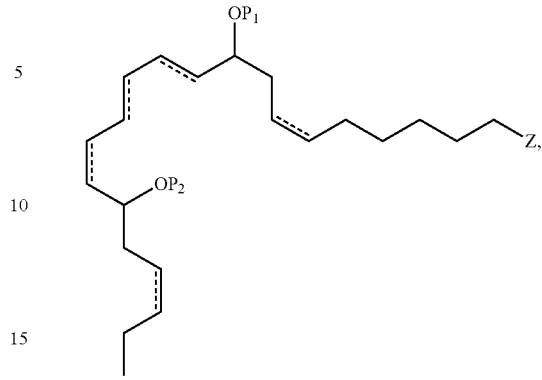
(Xa)
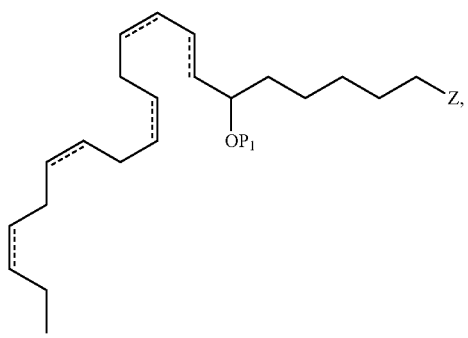
(VIIIa)
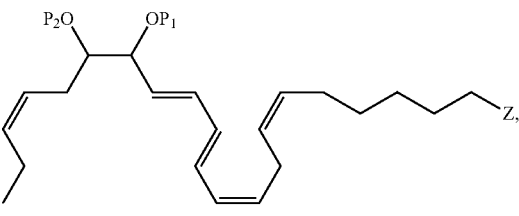
(XI)
PD2$_{n\text{-}3\,DHP}$
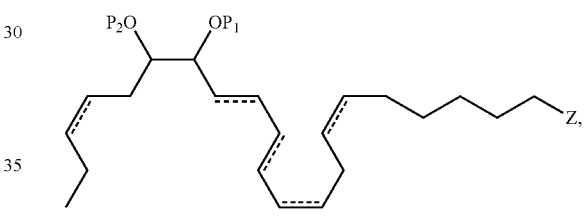
(XIa)
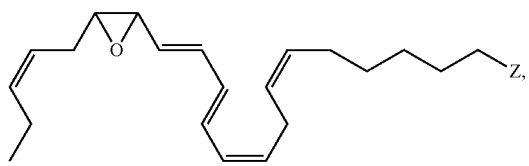
(IX)
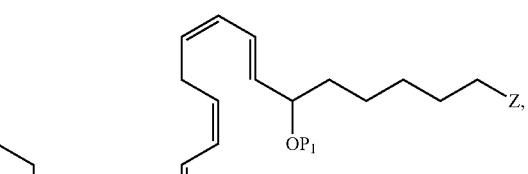
(XII)
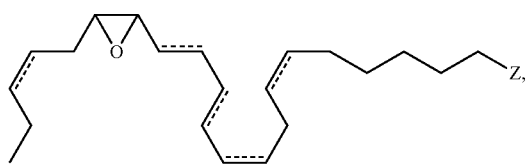
(IXa)
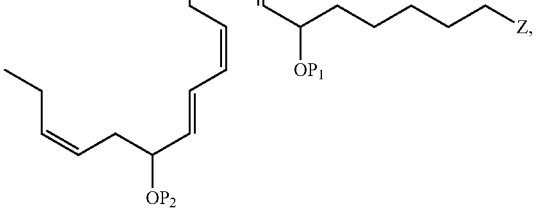
RVD5$_{n\text{-}3\,DPA}$
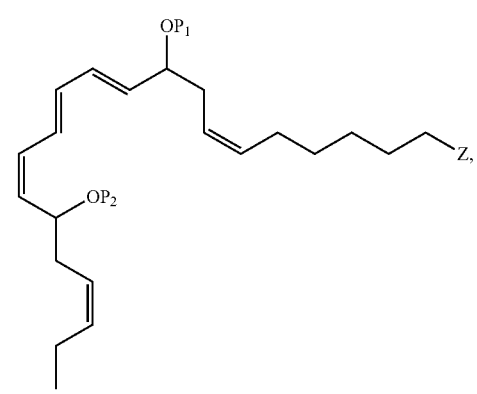
(X)
PD1$_{n\text{-}3\,DPA}$
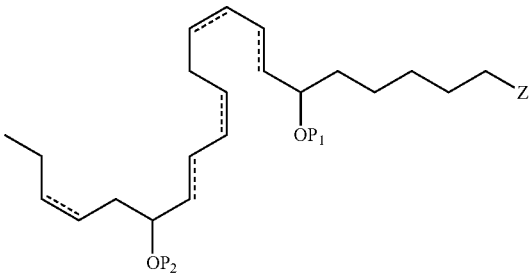
(XIIa)
wherein $P_1$, $P_2$, ═══, Z, $R^a$, $R^b$, $R^c$, $R^d$ and n are as previously defined, or a pharmaceutically acceptable salt thereof, provided when Z is —C(O)OR$^d$, then R$^d$ for Z is not a hydrogen when $P_1$ and $P_2$ are both hydrogen atoms. In one embodiment, $P_1$ and $P_1$ are both hydrogen atoms.

In other embodiments when compounds VIa through XIIa are purified, then $P_1$ and/or $P_2$ are both hydrogen atoms. In one aspect, Z is —C(O)OR$^d$ and R$^d$ of Z is a hydrogen atom. In another embodiment, $P_1$ and/or $P_2$ are both hydrogen atoms, Z is —C(O)OR$^d$ and R$^d$ of Z is a hydrogen atom.

It should be understood that compounds (VI) through (XIIa) include all pharmaceutically acceptable salts, esters thereof, the purified/isolated forms, as well as compounds wherein one or both of the possible hydroxyl groups are converted into a protecting group as described herein.

It should be understood that the intermediates described herein are also included as part of the invention and can be considered active agents as well. For example, ketone containing intermediates are within the scope of the active agents as well as alkyne intermediates as described herein.

Results and Discussion n-3 Docosapentaenoic Acid Products Exert Potent Anti-Inflammatory and Tissue Protective Actions In Vivo Since even minor changes in the structural properties of EFA are of functional significance,[22] it was investigated whether n-3 DPA, products that contain one fewer double bond than those derived from DHA (FIG. 1a), produced by exudate leukocytes exerted protective actions during acute inflammation. For this purpose, a model surgery-induced second organ injury was employed, the murine hind limb ischemia reperfusion model (FIG. 1b)[9]. Administration of an isolated mixture obtained via solid-phase extraction (see Methods) of the n-3 DPA products 10 min prior to onset of reperfusion led to protection from secondary organ injury as evidenced by reduction in lung tissue damage (FIG. 1c) and decrease in the number of infiltrated leukocytes into the lungs (~45%, p<0.05). These actions were comparable to protection afforded by the DHA-derived pro-resolving mediator RvD1 (FIG. 1c,d).

Assessment of whole blood neutrophil-platelet aggregates in these mice, a marker of systemic inflammation[24], following administration of n-3 DPA products or RvD1 gave a significant reduction (55-65%) in the levels of platelet-leukocyte aggregates found 2 h post reperfusion (FIG. 1e).

Using targeted lipid mediator metabololipidomics, it was next assessed whether these n-3 DPA products also regulated pro-inflammatory eicosanoid biosynthesis following ischemia reperfusion. Administration of these products led to a significant reduction in plasma prostanoid levels including $PGE_2$ (~75%) and thromboxane $B_2$ ($TxB_2$) (~80%; FIG. 1F). Here it was found that a significant reduction in plasma $LTB_4$ (~60%) levels along with a decrease in levels of its double di-oxygenation isomer 5S,12S-diHETE (~75%; FIG. 1g). Of note the n-3 DPA products displayed equal or higher potency at regulating plasma eicosanoid levels when compared to RvD1 (FIG. 1f,g). These results demonstrate that n-3 DPA products possess potent anti-inflammatory and tissue-protective actions, regulating leukocyte recruitment, pro-inflammatory mediator biosynthesis and systemic inflammation.

Targeted Metabololipidomics of Plasma Following Ischemia Reperfusion Injury

Having found that n-3 DPA products display potent actions during ischemia reperfusion, it was next investigated as to the role of endogenous n-3 DPA derived in the control of acute inflammation. First the plasma levels of unesterified arachidonic acid (AA), eicosapentaenoic acid (EPA), n-3 docosapentaenoic acid (DPA) and docosahexaenoic acid (DHA) were assessed in mice that were not subjected to an inflammatory stimulus. Plasma AA levels were 573.0 ng/ml, EPA levels were 116.2 ng/ml, n-3 DPA levels were 66.3 ng/ml and DHA levels were 146.1 ng/ml. Following ischemia reperfusion injury, circulating values for all 4 PUFA were elevated, with levels for n-3 DPA increasing ~12 times to those found in uninjured mice (FIG. 2a).

Figure 9:
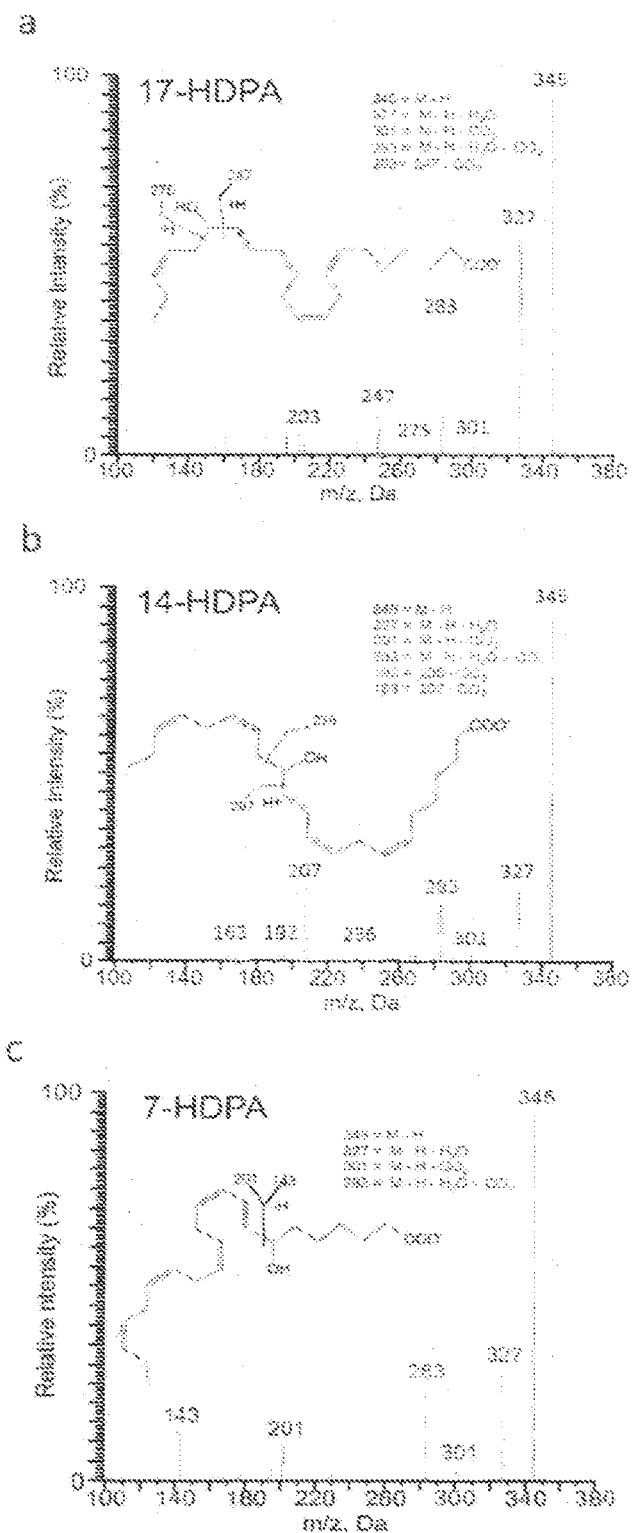
FIG. 9: MS-MS spectra employed for identification of n-3 DPA monohydroxy products in mouse plasma. Mice were subjected to ischemia reperfusion injury (see Methods for details). Two h into reperfusion, blood was collected via cardiac puncture and the plasma was obtained by centrifugation, products were extracted and n-3 DPA monohydroxy products were assessed by lipid mediator metabololipidomics. Representative MS-MS spectra used for identification of (a) 17-HDPA, (b) 14-HDPA, and (c) 7-HDPA. Results are representative of n=4.

Next evidence was sought for the conversion of n-3 DPA to bioactive mediators during acute inflammation. Using lipid mediator metabololipidomics and monitoring the precursor ion m/z 345 in Q1 and the product ion m/z 327 in Q3, three major products eluting in LC-peaks were found (FIG. 2b). Analysis of the tandem mass spectra (MS-MS) for the products under each peak demonstrated that peak I, at retention time ($R_T$)=17.1 min, corresponded to 17-HDPA (FIG. 9a), the peak at $R_T$=17.3 min (peak II) to 14-HDPA (FIG. 9b) and peak III at $R_T$=17.6 min corresponded to 7-HDPA (FIG. 9c). Quantification of these novel products by multiple reaction monitoring (MRM) in the plasma of uninjured mice and mice subjected to ischemia reperfusion demonstrated that all three products were elevated following ischemia reperfusion injury (FIG. 1c). These results demonstrate that during acute inflammation, systemic n-3 DPA levels are elevated, and this n-3 EFA is converted to novel oxygenated products.

Chiral Metabololipidomics of Endogenous n-3 DPA Products

Figure 10:
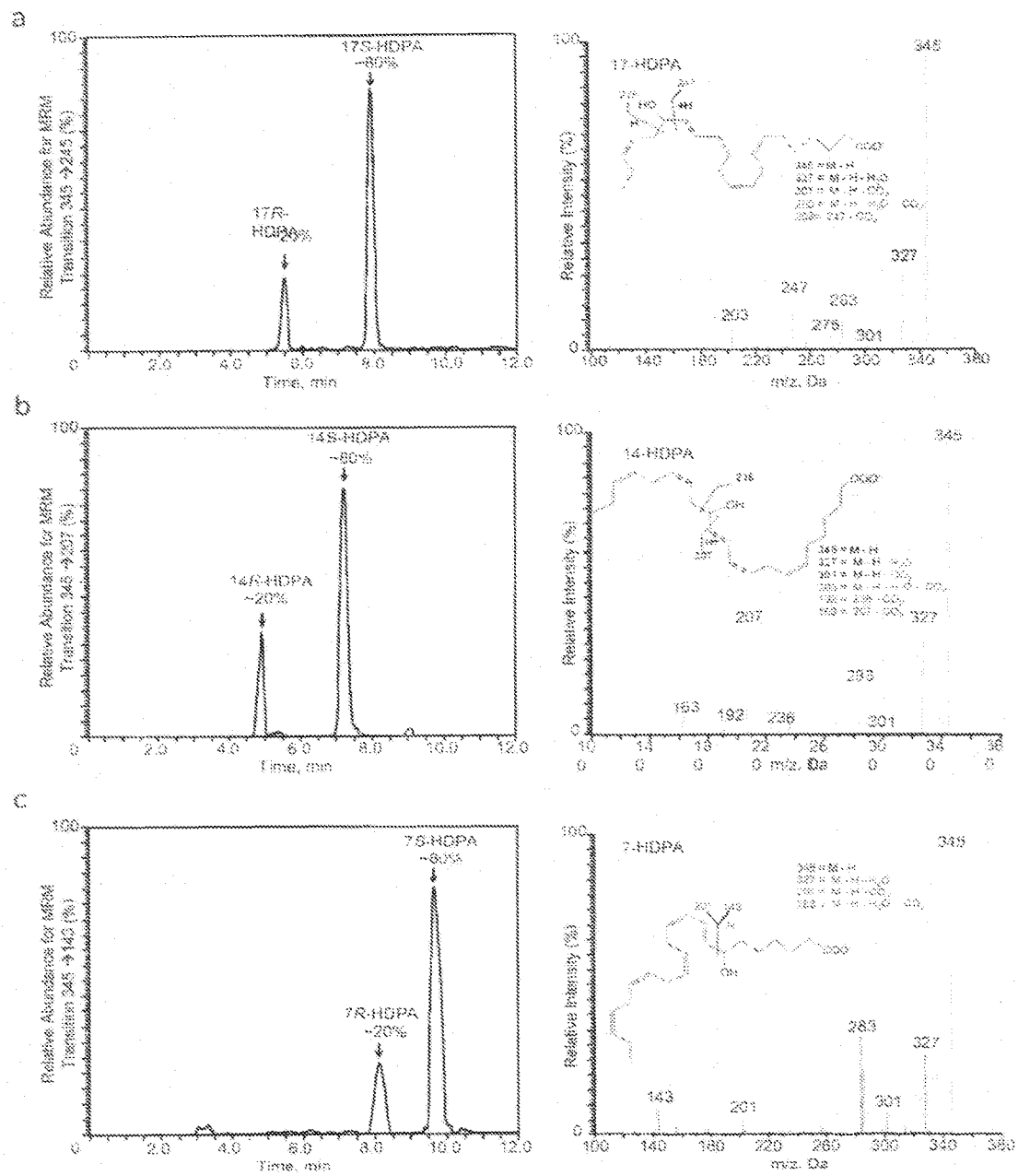
FIG. 10: Chiral lipid mediator metabololipidomics of isobaric monohydroxy-containing acids from n-3 DPA in murine plasma with ischemia reperfusion. In order to detect and quantify each positional isomer without ambiguity, an MRM method was established. Signature daughter ions for each monohydroxy acid (parent m/z, 345) were as follows: 17-HDPA-m/z 245, 14-HDPA m/z 207 and 7-HDPA-m/z 143. For each enantiomer pair, the R isomer was eluted before S isomers. The signature ion for each species was unique; only two (R and S isomers) peaks are present on each extracted ion chromatogram. Results are representative of n=3.

In order to elucidate the biosynthetic origins of these novel n-3 DPA-derived products chiral metabololipidomic profiling of the n-3 DPA products generated in vivo were designed. Reverse-phase chiral LC-MS-MS metabololipidomics of plasma samples obtained from mice subjected to ischemia reperfusion injury achieved baseline separation of 7R/S-HDPA, 14R/S-HDPA and 17R/S-HDPA (FIG. 10). Quantification of the two isomers for each of the products identified demonstrated that the R to S ratio for all of the monohydroxy products identified was ~20%:~80%. These results indicated that the conversion of n-3 DPA to these novel products is enzymatically regulated, since mammalian lipoxygenases are known to insert molecular oxygen in predominantly the S configuration[5].

Figure 11:
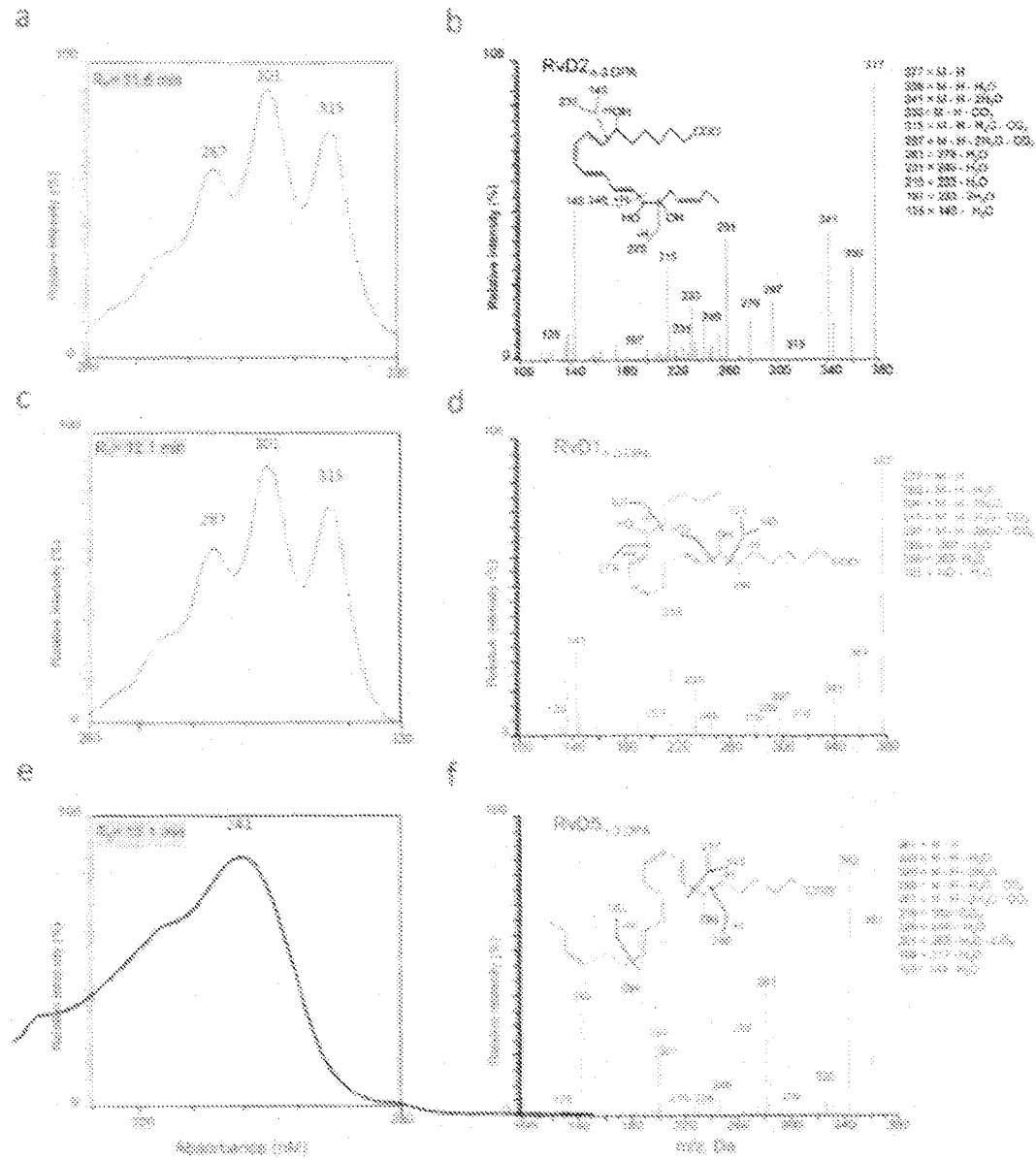
FIG. 11: n-3 DPA resolvins: physical properties. (a-f) HPLC retention times, online UV, fragment assignments shown in inset, and tandem mass spectra for (a,b) RvD2$_{n\text{-}3\ DPA}$, (c,d) RvD1$_{n\text{-}3\ DPA}$, and (e,f) RvD5$_{n\text{-}3\ DPA}$.
Figure 12:
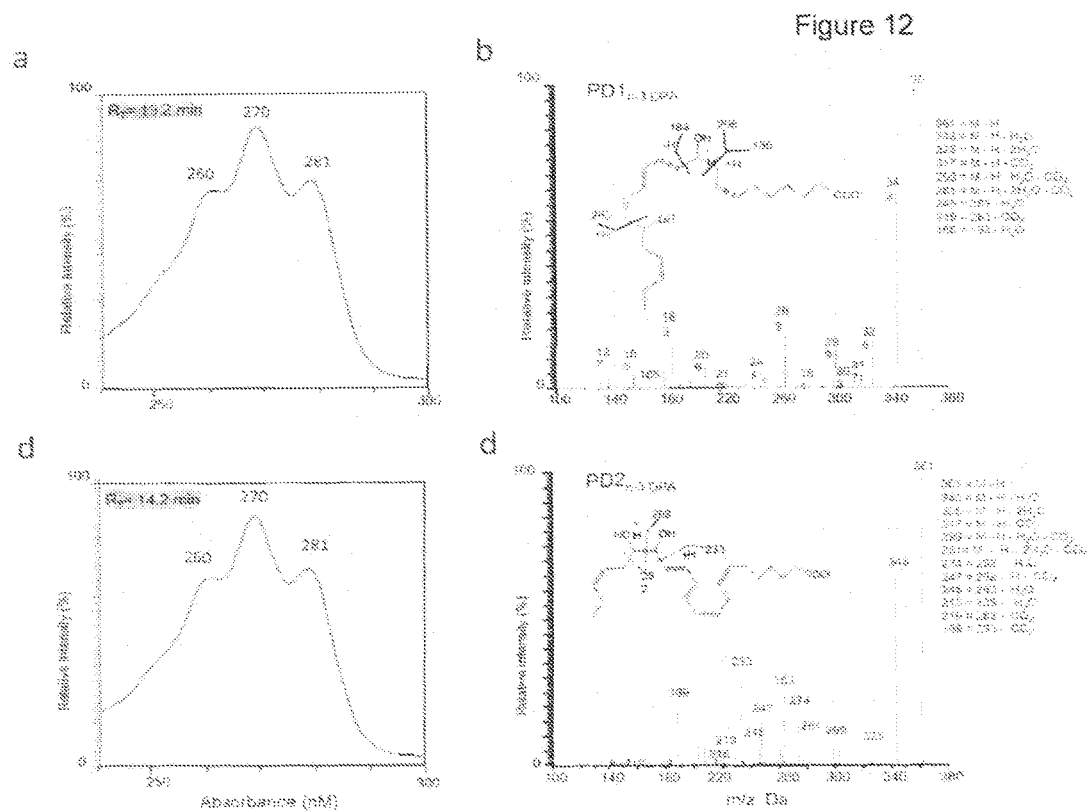
FIG. 12: n-3 DPA protectins: physical properties. (a-f) HPLC retention times, online UV, fragment assignments (inset), and tandem mass spectra for (a,b) PD1$_{n\text{-}3\ DPA}$ and (c,d) PD2$_{n\text{-}3\ DPA}$.

Targeted Metabololipidomics During Onset and Resolution of Acute Inflammation Uncovers Novel n-3 Docosapentaenoic Acid Products Having found that n-3 DPA is converted in vivo to yield monohydroxy acids that predominantly possess the S chirality, it was next investigated whether these n-3 DPA monohydroxy products were precursors and/or pathway markers for the biosynthesis of bioactive mediators. To this end, targeted LM metabololipidomics with plasma from mice subjected to ischemia reperfusion injury were employed. Multiple reaction monitoring of m/z 377 in Q1 and m/z 143 in Q3 yielded two peaks, the first at $R_T$=11.6 min and the second at $R_T$=12.1 min (FIG. 3a). Inspection of the MS-MS spectrum for the product eluting in peak at $R_T$=11.6 min demonstrated that this material corresponded to $RvD2_{n-3\ DPA}$ with the following characteristic ions assigned: m/z 307, m/z 279, m/z 249, m/z 233, and m/z 143 (cf. FIG. 11a,b); while assessment of the MS-MS spectrum for the products at $R_T$=12.1 min demonstrated that this material corresponded to $RVD1_{n-3\ DPA}$ (FIG. 3b). Multiple reaction monitoring of m/z 361 in Q1 and m/z 263 in Q3 yielded three peaks, one at $R_T$=13.6 min, the second peak with $R_T$=13.7 min and the third peak $R_T$=14.4 min (FIG. 3a). Assessment of MS-MS spectra for the product with $R_T$=13.6 min gave characteristic fragmentation corresponding to $RvD5_{n-3\ DPA}$ (FIG. 3c). MS-MS fragmentation for the material at $R_T$=13.7 min demonstrated characteristic fragmentation corresponding to $PD1_{n-3\ DPA}$ (FIG. 3d). The peak eluting at $R_T=14.4$ min was identified as $PD2_{n\text{-}3\ DPA}$ with the following characteristic ions assigned: m/z 233, m/z 247, m/z 189 (c.f. FIG. 12c,d). These findings demonstrate that n-3 DPA is converted to novel products that are cognate to pro-resolving mediators from DHA; therefore, the nomenclature from the DHA bioactive metabolome to describe each of these new structures was employed.

Figure 4:
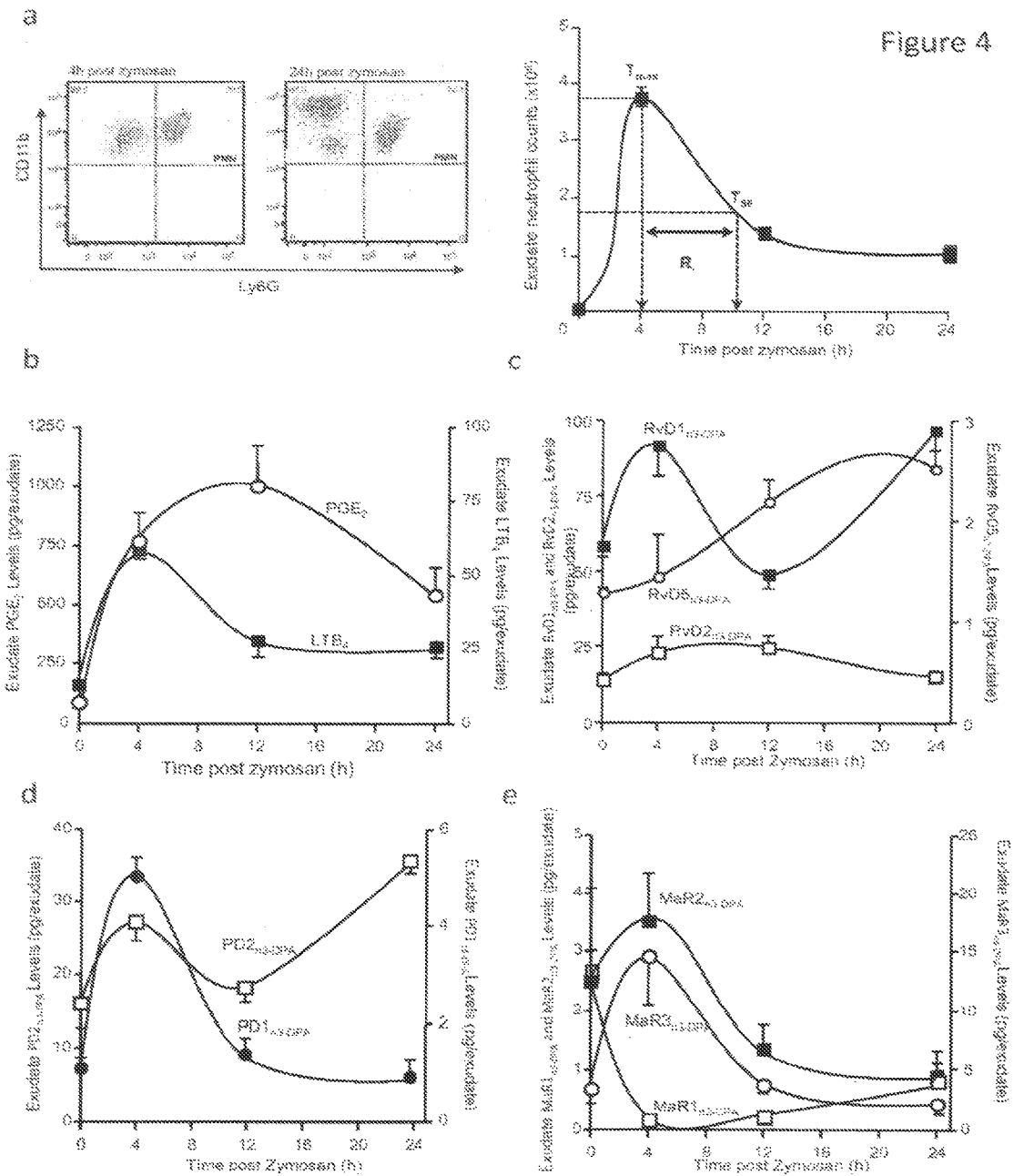
FIG. 4. Self-limited inflammation: Endogenous formation of novel immunoresolvents from n-3 DPA. Mice were treated with 0.1 mg zymosan i.p.; after the indicated time intervals peritoneal exudates were collected. (a) Exudate leukocyte counts obtained by light microscopy and flow cytometry. Exudate levels for (b) prostaglandin (PG) $E_2$ and leukotriene (LT) $B_4$; (c) resolvins, (d) protectins and (e) maresins were measured by lipid mediator metabololipidomics. Results are mean±SEM. n=4 mice per time point.

Since vascular leakage during inflammation supplies the site of inflammation with PUFA,[9] tissue levels of n-3 DPA products during the onset and resolution of inflammation were investigated. For this purpose, a self-limited model of inflammation was applied where, following the administration of a pro-inflammatory stimulus into the mouse peritoneum, there is a rapid recruitment of neutrophils into the site that peaks at around 6 h ($T_{max}$; FIG. 4a). This is followed by a decline in neutrophil numbers over the next 18 h. The time difference between $T_{max}$ and the point where neutrophil numbers reach 50% of maximum ($T_{50}$) is defined as the resolution interval $(R_i)$[25]. Using LM metabololipidomics, the levels of $LTB_4$ and $PGE_2$ were profiled that were rapidly produced during the initiation phase of the inflammatory response concomitant with neutrophil infiltration into the tissue (FIG. 4b). Maximal $LTB_4$ levels coincided with peak neutrophil infiltration, whereby $LTB_4$ levels rapidly subsided over the next 8 h. $PGE_2$ levels were also elevated early in the initiation phase of the response, with levels for this mediator persisting into the resolution phase. In this experimental setting, which characterizes the initiation and resolution phases of the inflammatory response[25] the profile of novel n-3 DPA products were determined in order to temporally stage each of these new products within the self-limited inflammatory response. It was found that endogenous production of $RvD1_{n\text{-}3\ DPA}$ and $PD2_{n\text{-}3\ DPA}$ displayed a bi-phasic profile, reaching a maximum during peak neutrophil infiltration and late into resolution (FIG. 4c,d). $PD1_{n\text{-}3\ DPA}$, $MaR2_{n\text{-}3\ DPA}$ and $MaR3_{n\text{-}3\ DPA}$ levels were each found to reach a maximum at the 4 h interval and gradually decreased over the next 20 h (FIG. 4 d,e). The peak in exudate $RvD2_{n\text{-}3\ DPA}$ levels coincided with the onset of resolution (the point where PMN levels reach ~50 of $T_{max}$). $RvD5_{n\text{-}3\ DPA}$ levels were found to gradually increase over the course of inflammation-resolution, with a maximum being reached late in the resolution phase. The n-3 DPA product corresponding to $MaR1_{n\text{-}3\ DPA}$ gave levels that were elevated in the peritoneum of naive mice, where upon challenge with zymosan these levels drastically decreased. Also, $MaR1_{n\text{-}3\ DPA}$ accumulated late during resolution (FIG. 4e). These results establish the endogenous production of novel n-3 DPA resolvins, protectins and maresins during acute inflammation and stage their formation primarily within the self-limited inflammatory response.

Specialized Pro-Resolving Mediators from n-3 DPA Exert Potent Anti-Inflammatory Actions In Vivo It was then determined whether these novel structures carried bioactivity. Intravenous administration of 100 ng of $RvD1_{n\text{-}3\ DPA}$ and $RvD2_{n\text{-}3\ DPA}$ significantly reduced neutrophil recruitment into the peritoneum (A; ~45%; FIG. 5a). In these experiments, it was found that the novel tri-hydroxy-containing n-3 DPA products significantly reduced exudate levels of the pro-inflammatory cytokines Interleukin (IL) 6 (~55%; FIG. 5b) and monocyte chemoattractant protein (MCP)-1 (~55%; FIG. 5c). Administration of the di-hydroxy-containing n-3 DPA products from both 17-hydroperoxy-DPA (HpDHA; $RvD5_{n\text{-}3\ DPA}$ and $PD1_{n\text{-}3\ DPA}$; B; ~47%) and 14-HpDPA ($MaR1_{n\text{-}3\ DPA}$ and $MaR2_{n\text{-}3\ DPA}$; C; ~50%) also significantly reduced PMN recruitment and pro-inflammatory cytokine levels in these exudates (FIG. 5a-c).

Human Leukocytes Produce n-3 DPA Immunoresolvents.

Figure 13:
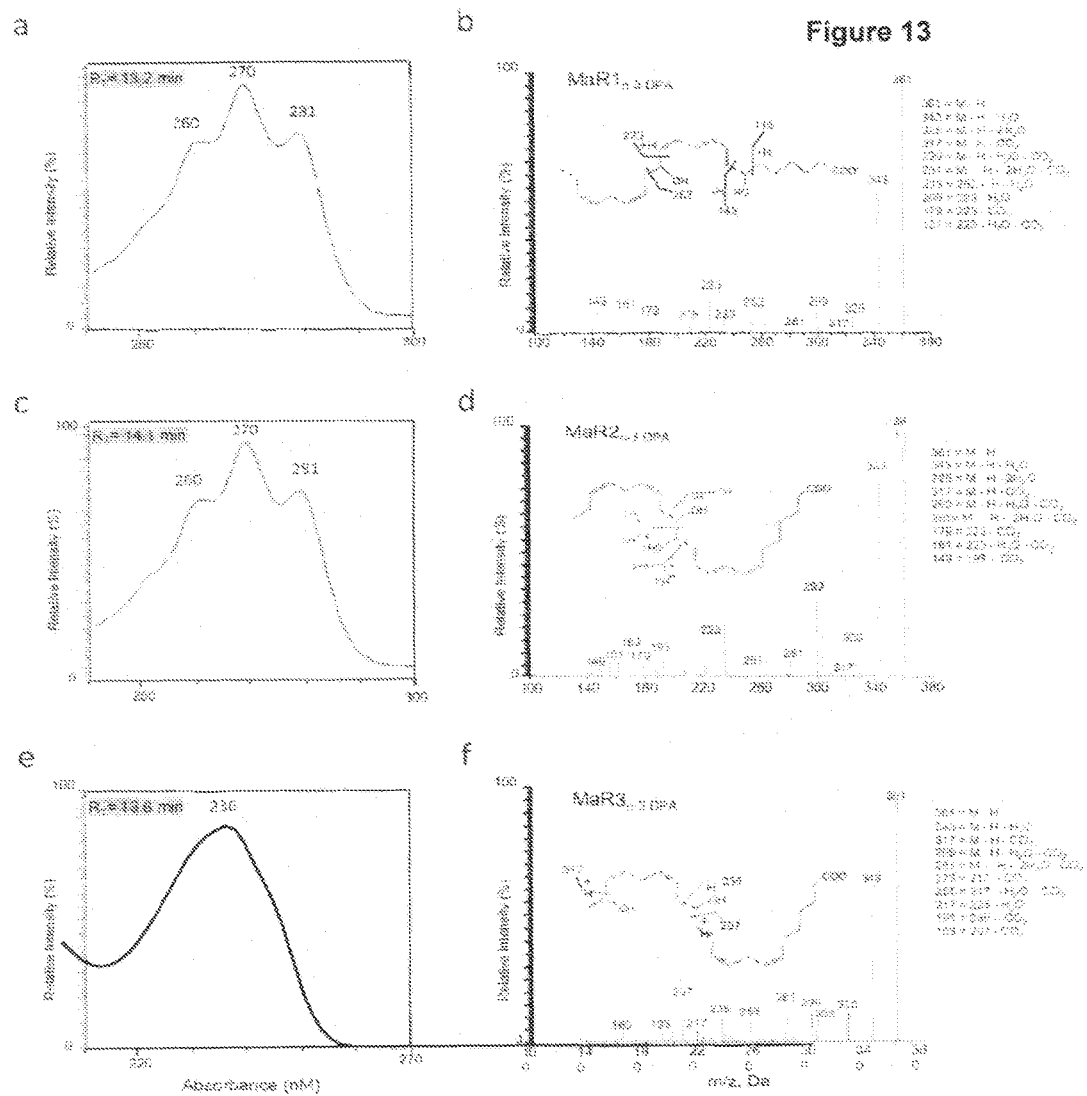
FIG. 13: n-3 DPA maresins: physical properties. (a-f) HPLC retention times, online UV, fragment assignments (inset), and tandem mass spectra for (a,b) MaR1$_{n\text{-}3\ DPA}$, (c,d) MaR2$_{n\text{-}3\ DPA}$, and (e,f) MaR3$_{n\text{-}3\ DPA}$.

Having found that these products are produced in murine systems, evidence was sought for their production by human leukocytes. Assessment of methyl formate fractions obtained from activated human peripheral blood neutrophils incubated with n-3 DPA by lipid mediator metabololipidomics profiling gave products that displayed chromatographic and MS-MS spectra consistent with resolvins, protectins and maresins that carry the n-3 DPA backbone (FIG. 5a). Assessment of the UV absorbance spectra and MS-MS fragments for each of the products gave fragment ions that were consistent with $RvD2_{n\text{-}3\ DPA}$ with m/z 377 [M-H], m/z 359 [M-H—$H_2O$] and m/z 333 [M-H—$CO_2$] (FIG. 5a and FIG. 11a,b). Additional diagnostic ions were identified at m/z 247, m/z 143 and m/z 279 consistent with the presence of hydroxy groups at carbon positions 7, 16 and 17. In the tri-hydroxy chromatographic regions, $RvD1_{n\text{-}3\ DPA}$ was identified as demonstrated by its characteristic fragmentation pattern and UV absorbance spectra, consistent with hydroxyl groups at the carbon 7, 8 and 17 positions (FIG. 3a,b and FIG. 11c,d). Assessment of the UV absorbance and MS-MS spectra in the di-hydroxy region revealed the presence of $RvD5_{n\text{-}3\ DPA}$ (FIG. 3a,c and FIG. 11e,f), $PD1_{n\text{-}3\ DPA}$ (FIG. 3a and FIG. 13a,b) and $MaR3_{n\text{-}3\ DPA}$ (FIG. 3a and FIG. 13e,f). Using LM metabololipidomics it was found that human monocyte-derived macrophages produce resolvins, protectins and maresins from endogenous n-3 DPA (n=3). These findings demonstrate that human leukocytes can convert both exogenous as well as endogenous n-3 DPA to novel n-3 DPA immunoresolvents.

n-3 DPA Products Exert Anti-Inflammatory and Pro-Resolving Actions on Human Leukocytes.

Figure 7:
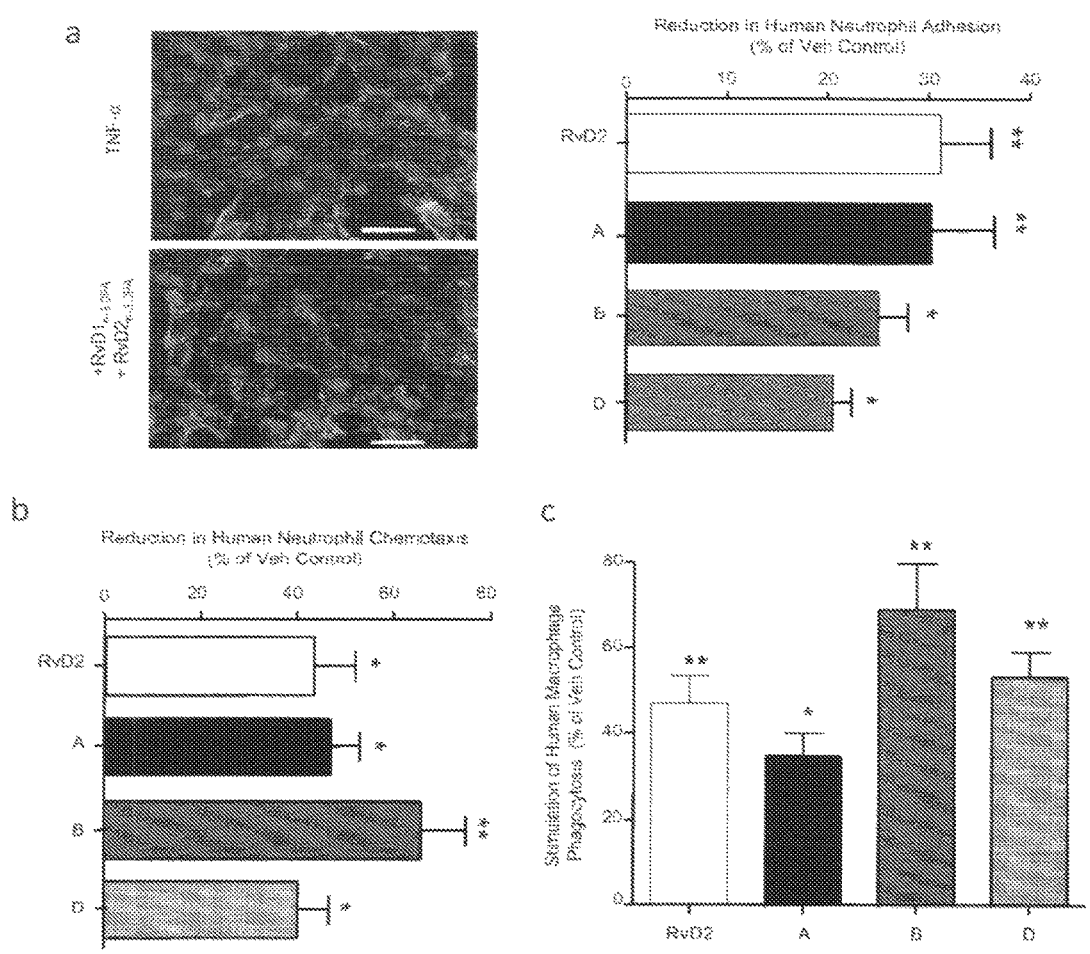
FIG. 7. Reduction in human neutrophil chemotaxis, neutrophil-endothelia cell adhesion and stimulation of macrophage phagocytosis by n-3 DPA-derived immunoresolvents. (a) Left panel: micrographs depict PKH26-labeled neutrophils adherent to WGA-Alexafluor® 488-labeled HUVEC stimulated with TNF-α (10 ng/ml, 4 h, 37° C., 0.1% FCS) with or without n-3 DPA resolvins (1 nM, 15 min, 37° C., pH7.45; ×40 magnification). Right panel: Fluorescently labeled human neutrophils were incubated with vehicle (0.1% EtOH in PBS) or n-3 DPA products. These were then added to TNF-α-stimulated HUVEC and incubated for 30 min (37° C.), non-adherent cells were washed and extent of neutrophil adhesion assessed using a SpectraMax M3 Plate reader. (b) Neutrophils were incubated with vehicle (0.1% EtOH in PBS) or n-3 DPA products (1 nM, 15 min, 37° C., pH7.45) prior to loading on ChemoTx chambers and assessing chemotaxis towards IL-8 (100 ng/ml, 90 min, 37° C., pH7.45). (c) Macrophages were incubated with vehicle (0.1% EtOH in PBS) or n-3 DPA products (1 nM, 15 min, 37° C., pH7.45) prior to addition of fluorescently labeled zymosan (1:10 macrophages to zymosan). After 60 min (37° C., pH7.45), the incubation was stopped, extracellular fluorescence quenched using trypan blue and phagocytosis assessed using a SpectraMax M3 Plate reader. The ratio of RvD1$_{n\text{-}3\ DPA}$ to RvD2$_{n\text{-}3\ DPA}$ (A) was ~3:1; the ratio of RvD5$_{n\text{-}3\ DPA}$ to PD1$_{n\text{-}3\ DPA}$ (B) was ~9:1; the ratio of PD1$_{n\text{-}3\ DPA}$ to PD2$_{n\text{-}3\ DPA}$ (C) was ~1:5; the ratio of MaR1$_{n\text{-}3\ DPA}$ to MaR2$_{n\text{-}3\ DPA}$ (D) was ~4:1. Results are mean±SEM. n=4 independent neutrophil and macrophage preparations (*P<0.05; **P<0.05 vs. vehicle incubated cells). Bar=50 µM.

It was next investigated whether these novel n-3 DPA products retained their leukocyte directed anti-inflammatory and pro-resolving actions when incubated with human leukocytes. A key step in neutrophil recruitment to the site of inflammation is firm adhesion to the vascular endothelium[26]. Incubation of neutrophils with $RvD1_{n\text{-}3\ DPA}$ and $RvD2_{n\text{-}3\ DPA}$, (A; ~30%), RvD5-n-3 DPA and $PD1_{n\text{-}3\ DPA}$, (B; ~25%) or $PD1_{n\text{-}3\ DPA}$ and $PD2_{n\text{-}3\ DPA}$ (C; ~22%) led to a significant reduction in neutrophil adhesion to TNF-α activated endothelial cells to a similar extent as RvD2 (~30%; FIG. 7a), a potent pro-resolving mediator[27].

Neutrophil-endothelial cell adhesion is mediated by adhesion molecules expressed on both the endothelial and neutrophil surface that are up-regulated during inflammation[26]. One of these adhesion molecules is Intercellular Adhesion Molecule 1 (ICAM-1/CD54) expressed on endothelial cells[28]. Incubation of each of the n-3 DPA products with endothelial cells prior to incubation with TNF-α also led to a significant reduction in endothelial cell ICAM-1 expression (~25-40%; FIG. 5b).

It was next questioned whether the n-3 DPA pro-resolving mediators regulated human peripheral blood leukocyte recruitment to a chemotactic stimulus. Incubation of human leukocytes with RvD2 led to a significant reduction in neutrophil (~42%) recruitment towards an IL-8 gradient. When human neutrophils were incubated with $RvD1_{n\text{-}3\ DPA}$ and $RvD2_{n\text{-}3\ DPA}$ (1 nM), we also found a significant reduction in neutrophil chemotaxis (~45%) towards an IL-8 gradient (FIG. 7b). Incubation of human neutrophils with 1 nM of the di-hydroxy containing products (i.e. $RvD5_{n\text{-}3\ DPA}$ and $PD1_{n\text{-}3\ DPA}$, C; or $MaR1_{n\text{-}3\ DPA}$ and $MaR2_{n\text{-}3\ DPA}$, D) also led to a significant reduction in neutrophil chemotaxis (~40-75%) towards IL8 (FIG. 7b).

Because macrophage clearance of cellular debris and apoptotic cells is a critical process in promoting the resolution of acute inflammation[1], human monocyte-derived macrophages were incubated with RvD2, which led to a significant increase in the uptake of opsonized zymosan particles (~50%; FIG. 7c). Addition of RvD5$_{n-3\,DPA}$ and PD1$_{n-3\,DPA}$, (1 nM) to macrophages each also led to a significant increase (~70%) in macrophage phagocytosis of fluorescently labeled zymosan (FIG. 7c). Macrophage incubations with MaR1$_{n-3\,DPA}$ and MaR2$_{n-3\,DPA}$ (~55%) or RvD1$_{n-3\,DPA}$ and RvD2$_{n-3\,DPA}$ (~45%) also gave significant increases in macrophage uptake of fluorescently labeled zymosan (FIG. 7c). These results demonstrate that the novel n-3 DPA mediators exert potent anti-inflammatory and pro-resolving actions with human leukocytes limiting human neutrophil recruitment and macrophage phagocytosis, key processes in promoting resolution and by definition those assigned to pro-resolving mediators[1,2].

Using lipid mediator metabololipidomics, novel n-3 DPA-derived products were identified and their biosynthesis was staged during self-limited inflammation in inflammatory exudates. With murine models of acute inflammation and human leukocytes, their anti-inflammatory, pro-resolving and tissue protective actions, were determined defining these novel n-3 DPA products as immunoresolvents.

In humans, circulating n-3 DPA levels do not appear to be directly associated with dietary intake, unlike other n-3 EFA including DHA and EPA[21,29], thus suggesting in humans a primary endogenous metabolic origin for n-3 DPA. Along these lines, a recent genome wide association study with more than 8500 participants from various ethnicities demonstrated that elevated plasma n-3 DPA levels are associated with single nucleotide polymorphisms in the genes encoding for the fatty acid elongase 2 (ELOVL2) and glucokinase regulatory protein (GCKR)[21]. This increase in n-3 DPA levels is also associated with a reduction in circulating DHA levels. Of interest, circulating n-3 DPA has been associated with protection from cardiovascular disease[30,31,32]. Hence, the present findings indicating that n-3 DPA is a precursor to new potent bioactive products may have wide implications in individuals carrying elevated circulating levels of n-3 DPA.

Ischemia-reperfusion injury is of considerable consequence in the pathology of many diseases including periodontal disease, arthritis and stroke as well as being of relevance during surgical procedures, in particular those involving extremities, causing aberrant leukocyte activation that results in local and remote tissue and organ damage[33]. Neutrophils in these settings play pivotal roles in the perpetuation of reperfusion injury giving rise to second organ injury[33]. However, phagocytes, including neutrophils when appropriately activated, are also instrumental in orchestrating resolution processes via their temporal production of pro-resolving mediators in resolving exudates[14,15,34,35]. Hence n-3 DPA products obtained from phagocytes collected from self-resolving exudates display potent protective actions from second organ injury during ischemia reperfusion have implications in a wide range of human pathologies. Indeed these products markedly reduced both local tissue damage and neutrophil infiltration into the lungs (FIG. 1), a hallmark of second organ injury, to a similar extent as the DHA-derived resolvin D1, a known potent pro-resolving mediator[9].

The formation of platelet-leukocyte aggregates in the vasculature is also a component of many inflammatory disorders including stroke, sepsis and hypertension. Formation of these microcellular aggregates enhances the production of a number of pro-inflammatory cytokines including IL-8 and MCP-1 as well as increases the levels of platelet aggregating factor, a potent pro-inflammatory lipid mediator (for a review, see ref[24]). In this context, elevated levels of circulating platelet-leukocyte aggregates are proposed as an early marker for acute myocardial infarction and are increasingly regarded as a cardiovascular risk factor[36]. In the present studies, administration of phagocyte-derived n-3 DPA products led to a reduction in circulating platelet-neutrophil aggregates following ischemia reperfusion injury. In addition, we also found a substantial reduction in plasma pro-inflammatory eicosanoid levels including LTB$_4$ and TxB$_2$ (FIG. 1), actions that were comparable to those afforded by DHA-derived RvD1. Therefore, these results demonstrate that n-3 DPA products display potent systemic anti-inflammatory and tissue protective actions.

Figure 2:
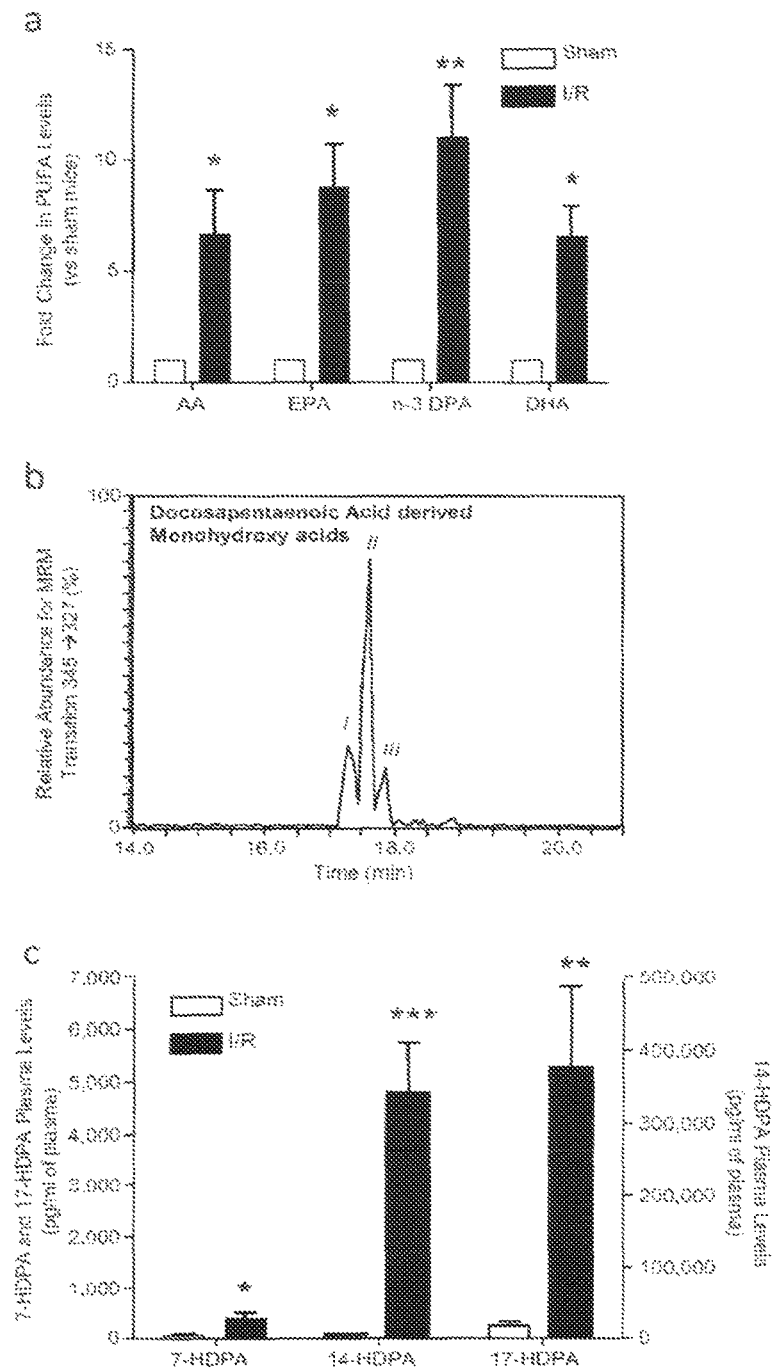
FIG. 2. n-3 DPA levels increase in acute inflammation and is converted to novel products in vivo. Mice were subjected to ischemia reperfusion injury (see Methods for details) at 2 h of reperfusion, blood was collected via cardiac puncture and plasma was obtained by centrifugation, products were extracted and monohydroxy n-3 DPA levels were assessed by lipid mediator metabololipidomics. (a) Plasma polyunsaturated fatty acid levels; (b) Representative chromatographs obtained by Multiple Reaction Monitoring (MRM) of the parent ion ($Q_1$) m/z 345 and a diagnostic daughter ion ($Q_3$) m/z 327. (c) Monohydroxy-containing levels in plasma of sham mice and mice subjected to I/R. Results for a and c are mean±SEM. n=4. Results for b are representative of n=4. *P<0.05; P<0.01; *P<0.01 vs. sham mice.
Figure 3:
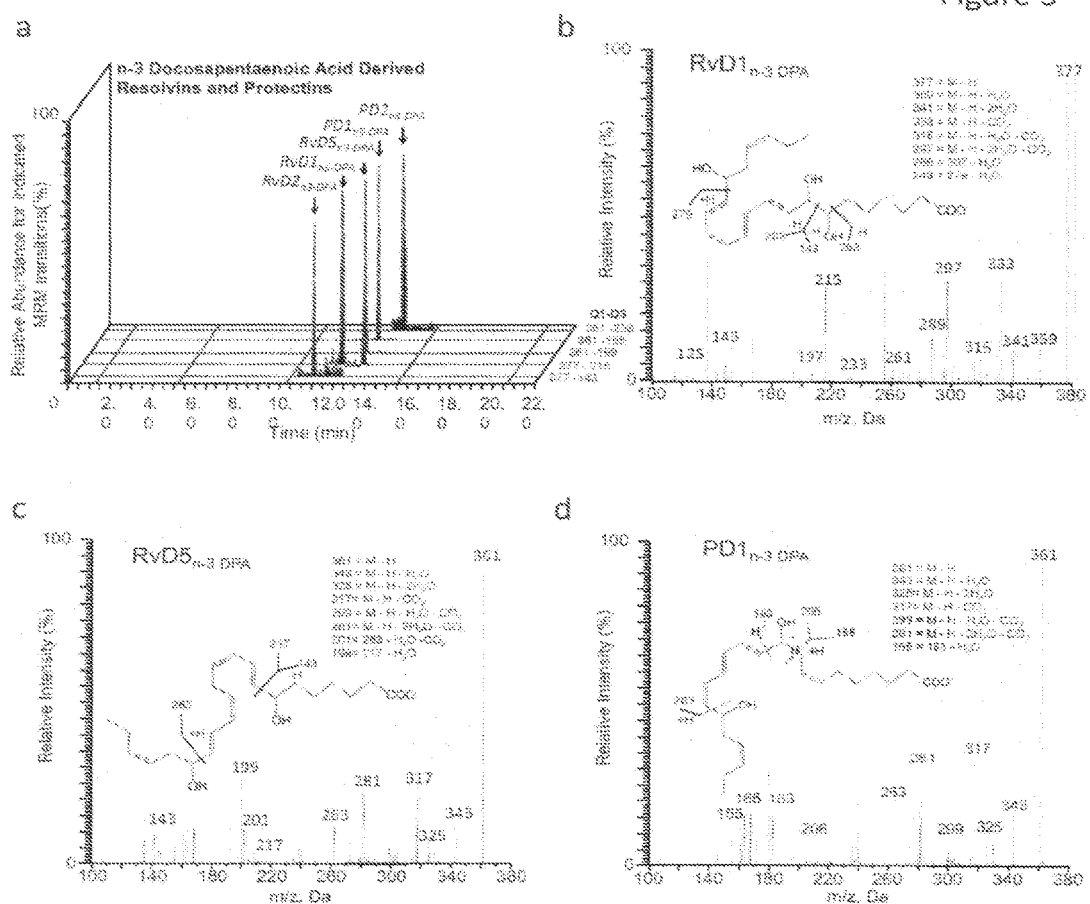
FIG. 3. Identification of novel endogenous n-3 DPA pro-resolving mediators. Mice were subjected to ischemia reperfusion injury (see Methods and FIG. 2 for details). Two h into reperfusion, blood was collected and lipid mediators identified by lipid mediator metabololipidomics. (a) Representative chromatographs obtained by Multiple Reaction Monitoring of the parent ion ($Q_1$) and a diagnostic daughter ion ($Q_3$) in the MS-MS of n3-DPA resolvins, protectins and maresins. Representative MS-MS spectra used for identification of (b) $RvD1_{n-3\ DPA}$, (c) $RvD5_{n-3\ DPA}$, and (d) $PD1_{n-3\ DPA}$. Results are representative of n=4.
Figure 6:
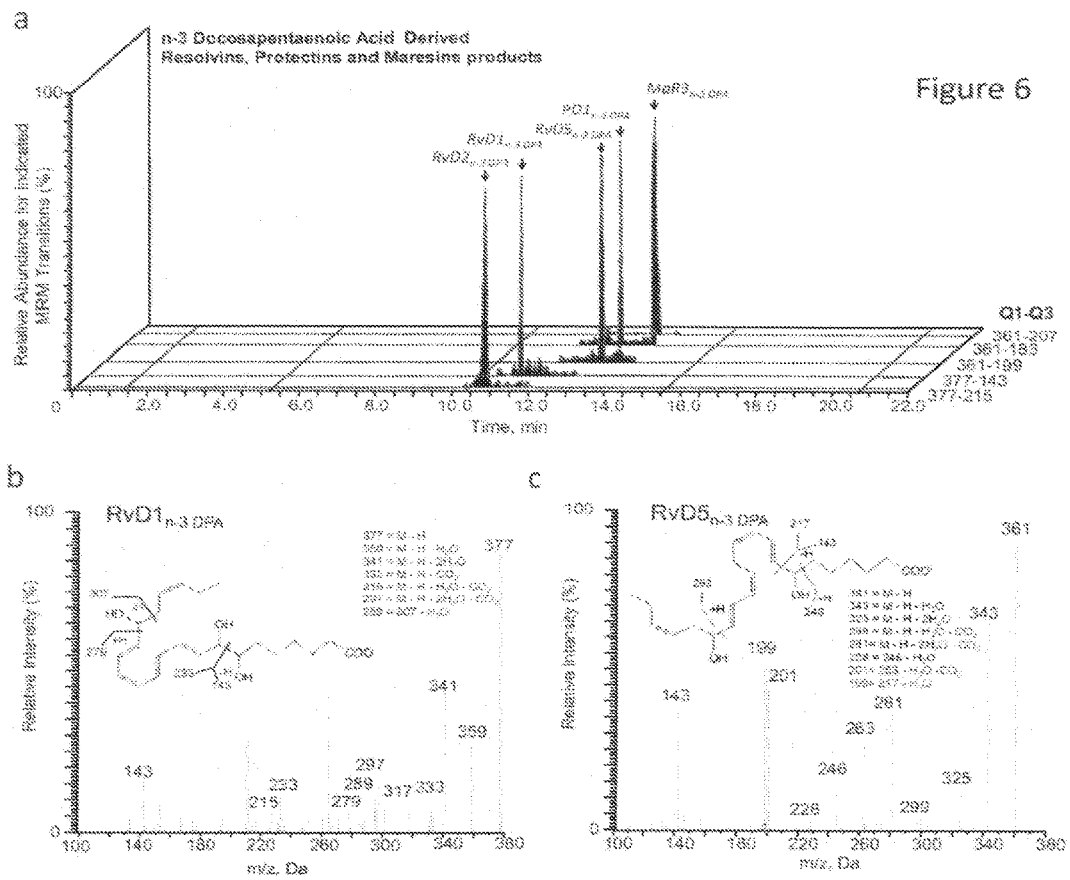
FIG. 6. Human neutrophils produce novel n-3 DPA-derived immunoresolvents. Human neutrophils were prepared from peripheral blood (see Methods for details), suspended in DPBS (80×10$^6$/ml) and incubated with serum treated zymosan (0.1 mg) and n-3 DPA (1 µM, 30 min, 37° C., pH 7.45); incubations were stopped with ice-cold methanol and products assessed by lipid mediator metabololipidomics. (a) Representative chromatographs obtained by Multiple Reaction Monitoring of the parent ion (Q$_1$) and a diagnostic daughter ion (Q$_3$) in the MS/MS. Representative MS/MS spectra used for identification of (b) RvD1$_{n\text{-}3\ DPA}$ and (c) RvD5$_{n\text{-}3\ DPA}$. Results are representative of n=4.

Phagocytes carry lipoxygenase enzymes that are involved in the biosynthesis of pro-resolving mediators[14,15,35]. These enzymes convert their substrate in a stereospecific manner, inserting molecular oxygen predominantly in the S configuration[5,34]. It was found that the systemic levels of n-3 DPA and the new n-3 DPA products (i.e. 17-HDPA, 14-HDPA and 7-HDPA) were each elevated during acute inflammation in vivo (FIG. 2). In addition, chiral lipidomics of these n-3 DPA products demonstrated that the hydroxy groups in these products were predominantly in the S configuration suggesting that each was produced via lipoxygenases (FIG. 10). Targeted metabololipidomics demonstrated that n-3 DPA is further oxygenated, in both murine in vivo and isolated human leukocytes, to products that are congenerous of the DHA-derived pro-resolving mediators (FIGS. 3, 6). In addition, endogenous levels of these novel n-3 DPA mediators were temporally regulated during self-limited inflammation suggesting that each may possess distinct roles in the regulation of inflammation-resolution and in organ protection (FIG. 4).

Figure 8:
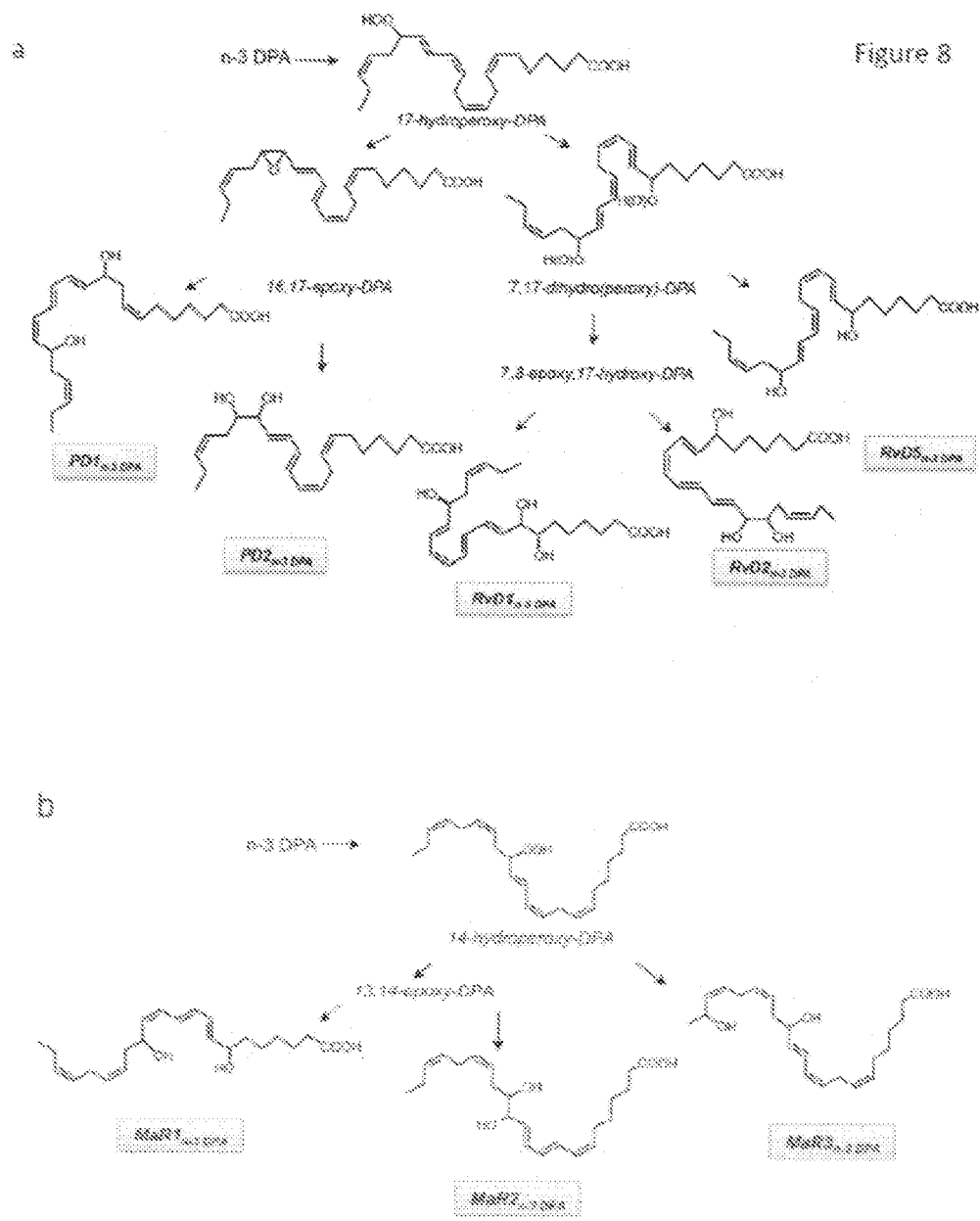
FIG. 8. Biosynthetic schemes proposed for novel n-3 docosapentaenoic acid products and their actions. At the site of injury, n-3 DPA is converted to (a) 17-HpDPA that undergoes further conversion by lipoxygenation to the n-3 DPA resolvins. 17-HpDPA is also a substrate for enzymatic conversion to an epoxide intermediate that is next enzymatically hydrolyzed to the n-3 DPA protectin structures. (b) n-3DPA is also converted to 14-lipoxygenation to yield 14-HpDPA that is further converted to an epoxide intermediate and then enzymatically hydrolyzed to MaR1$_{n\text{-}3\ DPA}$ and/or MaR2$_{n\text{-}3\ DPA}$. 14-HpDPA can also undergo a second oxygenation at the omega-1 position to yield the MaR3$_{n\text{-}3\ DPA}$. Note that each product is depicted in the 17S and 14S configuration based on the results obtained from chiral lipidomics that indicated S as the predominate form of each but may also carry 17R as well as 14R chirality from lipoxygenase reactions as these lesser components (see FIG. 10 and text for details). The complete stereochemistries of these novel mediators remain to be established and are depicted in their likely configuration based on biogenic synthesis (see FIGS. 11-13 for retention times, UV and MS-MS for each of these mediators).

In light of the results from the present studies in conjunction with earlier mechanisms proposed for the biosynthesis of the D-series resolvins, protectins[15,34] and maresins[35], the pathways for the novel n-3 DPA immunoresolvent are illustrated in FIG. 8. In this proposed scheme, n-3 DPA is first converted via 17 lipoxygenation to 17-hydroperoxy-8Z,10Z, 13Z,15E,19Z-docosapentaenoic acid (17-HpDPA). This intermediate can next undergo a second lipoxygenation by 5-lipoxygenase-like reaction to yield the 7,8,17-trihydroxy-9,11,13,15E,19Z-docosapentaenoic acid (RvD1$_{n-3DPA}$), 7,16,17-trihydroxy-8,10,12,14E, 19Z-docosapentaenoic acid (RvD2$_{n-3DPA}$) and/or 7,17-trihydroxy-8E,10,13,15E, 19Z-docosapentaenoic acid (RvD5$_{n-3DPA}$) In addition, 17-HpDPA can undergo enzymatic conversion to an epoxide intermediate that is next enzymatically hydrolyzed to either 10,17-dihydroxy-7Z,11,13,15,19Z-docosapentaenoic acid (PD1$_{n-3DPA}$) or 16,17-dihydroxy-7Z,10,13,14,19Z-docosapentaenoic acid (PD2$_{n-3DPA}$). In a parallel pathway, the arachidonate 12-lipoxygenase coverts n-3 DPA to 14-hydroperoxy-7Z,10Z,12E,16Z19Z-docosapentaenoic acid (14-HpDPA) that is further converted to an epoxide intermediate and then enzymatically hydrolyzed to yield 7,14-dihydroxy-8,10,12,16Z,19Z-docosapentaenoic acid (MaR1$_{n-3\,DPA}$) or 13,14-dihydroxy-7Z,9,11,16Z,19Z-docosapentaenoic acid (MaR2$_{n-3\,DPA}$). Alternatively, this 14-HpDPA can undergo a second oxygenation at the omega-1 position to yield 14,21-dihydroxy-7Z,10Z,12E,16Z,19Z-docosapentaenoic acid (MaR3$_{n-3\,DPA}$). Of note, since the S isomer of both 17-HDPA and 14-HDPA was identified, the reduction products of 17-HpDPA and 14-HpDPA, as the major products in inflamed tissues (FIG. 10), it is highly likely that the stereochemistry at these positions is retained in the biosynthesis of the novel n-3 DPA-derived resolvins, protectins and maresins. Of note, it is conceivable that the R-containing diastereomers of the n-3 DPA resolvins, protectins and maresins may also be of biological relevance in inflammation-resolution, since they were also obtained via lipoxygenation reaction albeit to lesser proportions than their corresponding R-containing products (see FIG. 10).

Figure 5:
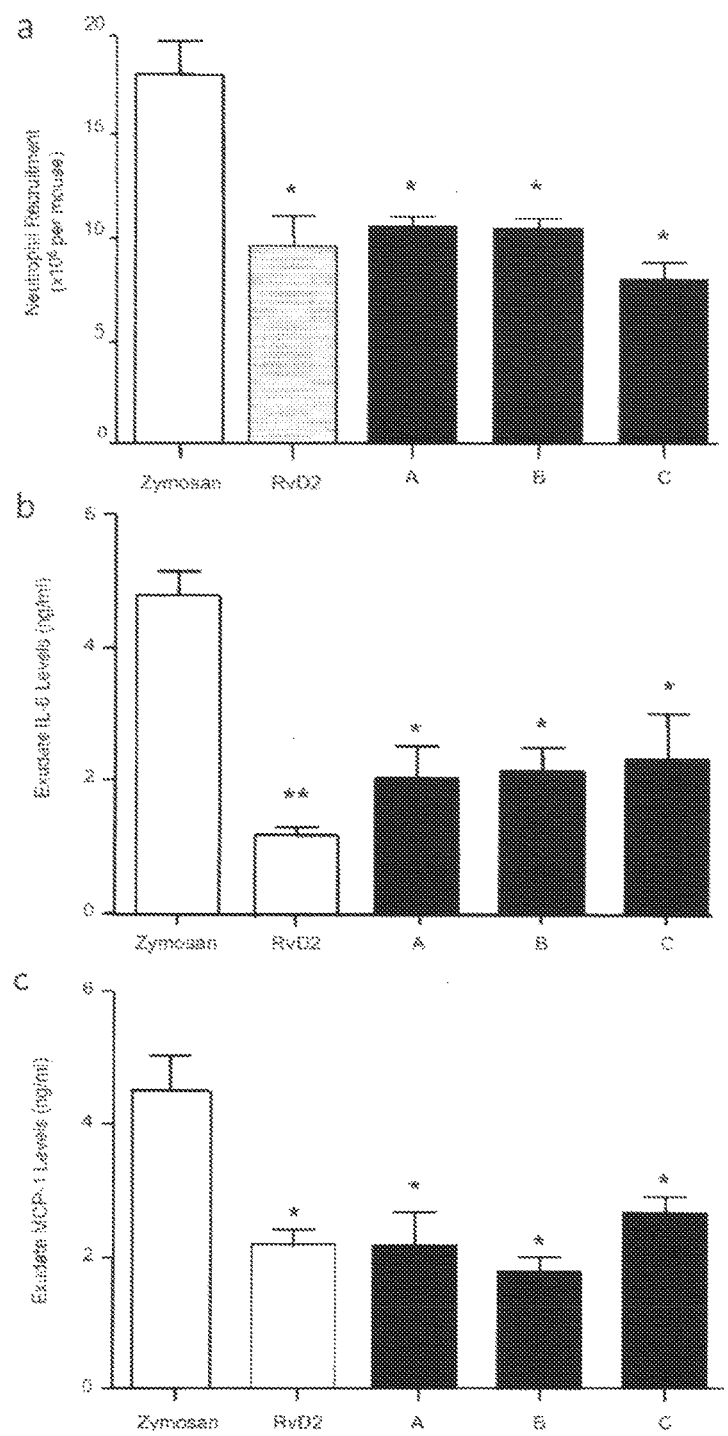
FIG. 5. n-3 DPA immunoresolvents display potent anti-inflammatory actions in vivo. The indicated n-3 DPA-derived product mixtures were administered by intravenous injection 10 min prior to the intraperitoneal administration of zymosan (0.1 mg, 500 μl PBS) to 6-8-week-old male FvB mice. At 4 h, peritoneal exudates were collected and the (a) number of infiltrated neutrophils was assessed by light microscopy and flow cytometry. Exudate levels for the pro-inflammatory mediators (b) IL6 and (c) MCP-1 were determined by cytokine array. The ratio of $RvD1_{n-3\ DPA}$ to $RvD2_{n-3\ DPA}$ was ~3:1 (A), the ratio of $MaR1_{n-3\ DPA}$ to $MaR2_{n-3\ DPA}$ was ~4:1 (B); the ratio of $RvD5_{n-3\ DPA}$ to PD1$_{n\text{-}3\ DPA}$ was ~9:1 (C). Results are mean±SEM. n=4 mice per group (*P<0.05; vs. vehicle group). Results are mean±SEM. n=4. *P<0.05, **P<0.01 vs. zymosan mice.
Figure 14:
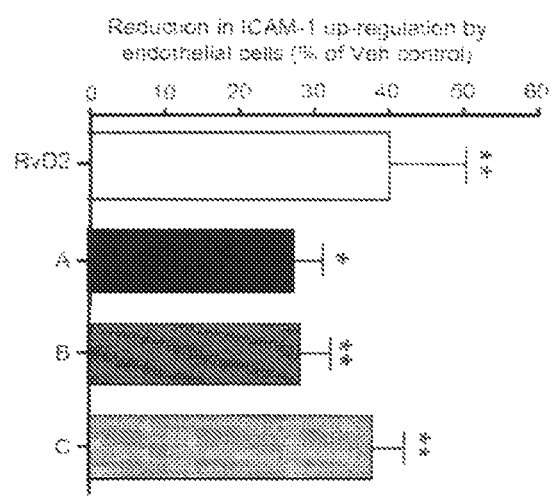
FIG. 14: n-3 DPA specialized pro-resolving mediators regulate endothelial ICAM-1 expression. HUVEC were incubated with vehicle (0.1% EtOH in PBS) or n-3 DPA products (1 nM, 15 min, 37° C., pH7.45) and then incubated with TNF-α (10 ng/ml, 4 h, 37° C., 0.1% FSC). ICAM-1 levels were then assessed by flow cytometry using a fluorescently labeled mouse anti-human ICAM-1 antibody. The ratio of RvD1$_{n\text{-}3\ DPA}$ to RvD2$_{n\text{-}3\ DPA}$ (A) was ~3:1; the ratio of RvD5$_{n\text{-}3\ DPA}$ to PD1$_{n\text{-}3\ DPA}$ (B) was ~9:1; the ratio of PD1$_{n\text{-}3\ DPA}$ to PD2$_{n\text{-}3\ DPA}$ (C) was ~1:5. Results are mean±SEM. n=4 independent neutrophil and endothelial cell preparations (*P<0.05; **P<0.05 vs. vehicle incubated cells).

Excessive neutrophil activation and infiltration to the inflamed site can be detrimental since it may lead to further tissue damage and propagation of the inflammatory response[4, 13]. When administered in vivo, $RvD1_{n-3\ DPA}$, $RvD2_{n-3\ DPA}$, $RvD5_{n-3\ DPA}$, $PD1_{n-3\ DPA}$, $MaR1_{n-3\ DPA}$, and $MaR2_{n-3\ DPA}$ each reduced neutrophil infiltration in murine peritonitis (FIG. 5). These mediators also demonstrated potent cytokine counter-regulatory actions reducing exudate levels of IL-6 and MCP-1 (FIG. 5) to levels comparable with the pro-resolving mediator RvD2[27]. The novel n-3 DPA immunoresolvents were also found to exert potent anti-inflammatory actions with human neutrophils and endothelial cells regulating central steps in the leukocyte recruitment cascades, reducing neutrophil chemotaxis and adhesion to endothelial cells (FIG. 7) as well as expression of the adhesion molecule ICAM-1 by endothelial cells (FIG. 14). Importantly, these mediators were found to enhance macrophage phagocytosis, a key process in accelerating the onset or resolution (FIG. 7)[1, 4, 37]. Thus, the actions for each of these novel n-3 DPA products are in accord with the key characteristic that define an immunoresolvent, a property shared with their DHA resolution metabolome SPM counterparts.

Since mammals lack enzymes that can insert double bonds in either the n-3 or n-6 position to polyunsaturated fatty acids, the precursor molecules for the production of n-3 and n-6 essential fatty acids, namely alpha linolenic acid (ALA) and linoleic acid (9Z,12Z-octadecadienoic acid), must be obtained via dietary intake[12]. In mammalian tissues, ALA is converted by elongation and desaturation to EPA and DHA. Linoleic acid on the other hand is converted, in a parallel pathway in humans, to arachidonic acid and subsequently to n-6 DPA[10, 12]. Thus, while n-3 DPA and n-6 DPA each share the carbon 22 and five unsaturated double bonds, their structures are different because they are produced via separate biosynthetic pathways from chemically dissimilar precursors and each possesses distinct biophysical properties[22]. Earlier, oxygenated products obtained from n-6 DPA were found to reduce neutrophil recruitment in a model of dermal inflammation[38], enhance macrophage phagocytosis[39], reduce ear swelling in a model of delayed type hypersensitivity[38] and protect against intestinal damage in a mouse model of intestinal inflammation[39], albeit displaying lower potency then the n-3 pro-resolving mediators[1] as well as compared to the new n-3 DPA mediators described herein. This is in accord with the finding that even subtle differences in the stereochemistry of lipid mediators can result in dramatic changes in their potency[34].

In summary, the structures of new n-3 DPA-derived products, their formation from endogenous sources, staged the production of each of these novel mediators during-inflammation resolution and determined their anti-inflammatory, pro-resolving and tissue protective properties are established. These actions are characteristic of specialized pro-resolving mediators[37] and define these novel n-3 DPA products as immunoresolvents. In view of the role of lipid mediators in inflammation and its timely resolution,[1, 4, 37] the n-3 DPA metabolome documented herein may mediate some of the beneficial actions associated with probiotic dietary supplementation[40]. Moreover, these new n-3 immunoresolvents may also serve as a compensatory mechanism in people with elevated n-3 DPA levels and lower circulating DHA levels[21] to compensate for losses in DHA SPM-regulated leukocyte-mediated tissue damage and timely resolution of acute inflammation.

Materials and Methods

Materials

Zymosan A, bovine serum albumin (BSA), Roswell Park Memorial Institute media 1640 (RPMI 1640), DPBS and Histopaque 1077-1 were purchased from Sigma-Aldrich. Rat anti-mouse Ly6G (clone 1A8; BD Biosciences); rat anti-mouse F4/80 (clone: BM8), CD11b (clone: Mac-1) and CD41 (clone: eBioMWReg30) were from eBioscience. Human recombinant granulocyte-monocyte colony stimulating factor (GM-CSF) and LC grade solvents were purchased from Fisher Scientific; Agilent Eclipse C18 (4.6 mm×100 mm×1.8 µm; 4.6 mm×50 mm×1.8 µm) column; C18 SPE columns (Biotage); fluorescently conjugated Zymosan A (Invitrogen); LC-MS-MS quantification and deuterated internal standards ($d_8$-5S-hydroxyeicosatetraenoic acid ($d_8$-5S-HETE), $d_4$-LTB$_4$, $d_5$-lipoxin A$_4$ ($d_5$-LXA$_4$), $d_4$-PGE$_2$, RvD1, RvD2; Cayman Chemicals).

Animals

All animals used in the present study were male FVB mice (Charles River Laboratories) that were 6-8 weeks old (weighing 20-25 g). They were maintained in a temperature- and light-controlled environment and had unlimited access to water and food (laboratory standard rodent diet 5001 (Lab Diet)), containing 1.5% eicosapentaenoic acid, 1.9% DHA of total fatty acids. Experiments were performed in accordance with the Harvard Medical School Standing Committee on Animals guidelines for animal care (Protocol 02570).

n-3 DPA-Derived Mediator Preparations

Exudates were obtained from mice 12 h after zymosan administration and incubated with n-3 DPA in DPBS (1 µM, 45 min, 37° C., pH 7.45); the incubations were stopped using 2 volumes of ice-cold methanol and products extracted as outlined in the sample extraction and lipid mediator metabololipidomics section below.

14S-HpDPA was prepared from n-3 DPA (~150 µM) incubated with 5.4 U/ml isolated 12-lipoxygenase (LOX) (porcine) (0.05 M phosphate buffer, 0.02% Tween 20, pH 7.4). 14S-HpDHA was isolated via RP-HPLC (1100 Series; Agilent Technologies) using a C18 column and a mobile phase consisting of methanol/water (60:20, vol/vol) at 0.5 ml/min that was ramped up to 98:2 vol/vol over for 20 min. Reduction with NaBH$_4$ yielded 14S-HDPA used for mass spectrometry standard. In determined incubations 14S-HpDPA was incubated with human macrophages (40×10$^6$/ml) or neutrophils (80×10$^6$/ml) in PBS (containing calcium and magnesium) and serum treated zymosan (StZ, 0.1 mg/ml); the incubations were stopped after 45 min and products extracted.

17S-HpDPA was prepared from n-3 DPA (~150 µM) incubated with 100 U/ml isolated soybean-LOX (Borate buffer, 4° C., pH 9.2). 17S-HpDHA was isolated via RP-HPLC. Reduction with NaBH$_4$ yielded 17S-HDPA used for mass spectrometry standard. Biogenic synthesis of the di- and tri-dioxygenation products was performed with 5-LOX enzyme (200 U/ml) incubated with 17S-HpDPA. In determined incubations, 17HpDPA was added to human macrophages (40×10$^6$/ml) or neutrophils (80×10$^6$/ml) in PBS (containing calcium and magnesium) and cells were then incubated with StZ (0.1 mg/ml), incubations were stopped after 45 min and products extracted. These were scaled up for direct comparison of biological and physical properties with other novel compounds isolated from peripheral blood leukocytes or inflammatory exudates.

Ischemia Reperfusion Injury

Mice were anesthetized by intraperitoneal injection of a mixture of xylazine (80 mg/Kg) and ketamine (10 mg/Kg). Hind-limb ischemia was initiated using tourniquets consisting of a rubber band placed on each hind limb as in[9]. Ten min prior to the initiation of reperfusion n-3 DPA products (obtained as described above) or Resolvin D1 (0.5 ng) were administered by intravenous injection and compared to vehicle alone. At the end of this reperfusion period (2 h), mice were euthanized and blood collected via cardiac puncture, lungs harvested, frozen in liquid nitrogen and stored at −80° C. or stored in 10% (v/v) buffered formalin and processed for histology by the Children's Hospital Boston Core Histology Facility. The frozen lungs were homogenized from individual mice, centrifuged and the tissue myeloperoxidase (MPO) levels were determined using a mouse MPO ELISA (R&D Systems.).

To investigate platelet leukocyte aggregates in murine whole blood after ischemia reperfusion, blood was collected 2 h post reperfusion by cardiac puncture and incubated with PE conjugated rat anti-mouse Ly6G and FITC conjugated rat anti-mouse CD41 or relevant isotype controls for 30 min at 4° C. Red blood cells were lysed using ice-cold red-blood cell lysis buffer (BD Biosciences) and cells fixed with 1% formalin prior to analysis by a BD Canto II. Data was analyzed using FlowJo (TreeStar Inc.).

Sample Extraction and Lipid Mediator Metabololipidomics.

All samples for LC-MS-MS analysis were extracted on SPE columns as in[41]. Prior to extraction, 500 pg of deuterium-labeled internal standards $d_8$-5S-HETE, $d_4$-LTB$_4$, $d_5$LXA$_4$ and $d_4$PGE$_2$ were added to facilitate quantification of sample recovery.

The LC-MS-MS system, QTrap 5500 (ABSciex), was equipped with an Agilent HP1100 binary pump and diode-array detector (DAD). An Agilent Eclipse Plus C18 column (100 mm×4.6 mm×1.8 μm) was used with a gradient of methanol/water/acetic acid of 60:40:0.01 (v/v/v) to 100:0:0.01 at 0.4 ml/min flow rate. To monitor and quantify the levels of the various LM, a multiple reaction monitoring (MRM) method was developed with signature ion fragments for each molecule. Identification was conducted using published criteria[17] with at least six diagnostic ions. Calibration curves were obtained using synthetic LM mixture ($d_8$-5S-HETE, $d_4$LTB$_4$, $d_5$LXA$_4$, $d_4$PGE$_2$, RvD1, RvD2, RvD5, Protectin (PD)1, Maresin 1 (MaR1), 17-hydroxydocosahexaenoic acid (17-HDHA), 14-hydroxydocosahexaenoic acid (14-HDHA) and 7-hydroxydocosahexaenoic acid (7-HDHA) at 1, 10, 100, 275 pg. Linear calibration curves for each were obtained with $r^2$ values in the range 0.98-0.99. Quantification was carried out based on peak area of the Multiple Reaction Monitoring (MRM) transition and the linear calibration curve for each compound. Where calibration curves for a structurally related DHA-derived product were not available (14,21-diHDPA, 13,14-diHDPA and 16,17-diHDPA), levels were monitored using a compound with similar physical properties.

For chiral lipidomic analysis, a Chiralpak AD-RH column (150 mm×2.1 mm×5 μm) was used with isocratic methanol/water/acetic acid 95:5:0.01 (v/v/v) at 0.15 ml/min. To monitor isobaric monohydroxy docosapentaenoic acid levels, a multiple reaction monitoring (MRM) method was developed using signature ion fragments for each molecule.

Zymosan Peritonitis

Zymosan (0.1 mg) was injected intraperitoneally (i.p.) in 1 ml of sterile saline. Exudates were collected at 0, 4, 12 and 24 h post zymosan. Leukocyte numbers and differential counts in the peritoneal exudates were determined as in[16]. In designated experiments, mice were administered intravenously (i.v): Vehicle (saline containing 0.1% EtOH), or the indicated mixture of n-3 DPA-derived products at 100 ng/mouse 5 min prior to i.p. zymosan administration (0.1 mg). After 4 h the exudates were collected and the number of extravasated neutrophils determined using Turks solution and flow cytometry as above.

Neutrophil Isolation and Chemotaxis

Peripheral blood neutrophils were obtained from healthy volunteers as in[17]. Briefly, neutrophils were prepared following density separation by layering on Ficoll-Histopaque 1077-1. The cells were then centrifuged at 300 g (30 min, 4° C.), and contaminating red blood cells were lysed by hypotonic lyses. These were then suspended at 1×10$^6$ cells/ml in DPBS containing 0.1% BSA and incubated with vehicle (0.1% EtOH in DPBS), RvD2 (1 nM) or the indicated mixtures of n-3 DPA-derived products (1 nM) for 15 min at 37° C. 2.5×10$^4$ cells were then added to the upper chamber of the ChemoTx System (3 μm pore size filter) and chemotaxis towards IL8 (100 ng/ml) was assessed (90 min, 37° C., 5% CO$_2$). The number of cells migrated into the bottom chamber was determined using Alama Blue following manufacturer's instructions on a Spectra Max M3 microplate reader (Molecular Devices Inc., Sunnyvale, Calif.).

Human Neutrophil-Endothelial Cell Adhesion

HUVEC were purchased from Lonza and cultured to passage 4. The cells were plated onto 96-well plates (Costar) coated with 1% gelatin and incubated overnight. The HUVEC were then incubated with TNF-α (10 ng/ml, 4 h, 37° C.) in media containing 0.1% fetal bovine serum. Human peripheral blood neutrophils were isolated as described above and labeled with CFDA as in[17]. These were then suspended in DPBS and incubated with vehicle (0.1% EtOH) or the indicated mixture of n-3 DPA products (1 nM, 37° C., pH 7.45). After 15 min the PMN (1×10$^5$) were added to the HUVEC and incubated for 60 min (37° C.). The plates were then washed with DPBS to remove non-adherent cells and the number of adherent neutrophils assessed using a Spectra Max M3 microplate reader.

Endothelial Cell Adhesion Molecule Expression

HUVEC were plated onto 1% gelatin coated 12-well plates and incubated overnight. Cells were then incubated with vehicle (0.1% EtOH in DPBS) or the indicated mixture of n-3 DPA products for 15 min. The HUVEC were then incubated with TNF-α (10 ng/ml, 37° C.) for 4 h. At the end of these incubations, ICAM-1 levels were assessed by flow cytometry following staining with fluorescently conjugated mouse anti-human ICAM-1 antibody (Clone HCD54; BioLegend) using the staining protocol[17].

Macrophage Preparation and Phagocytosis

Macrophages were prepared and phagocytosis was assessed as in[16]. Briefly, cells were incubated with vehicle (0.1% EtOH in DPBS), RvD2 (1 nM) or the indicated n-3 DPA products (1 nM) for 15 min at 37° C., then FITC-labeled zymosan was added and cells incubated 60 min at 37° C. Phagocytosis was assessed using an M3 SpectraMax plate reader.

Statistics

All results are expressed as means±SEM. Differences between groups were compared using Student's t test (2 groups) or 1-way ANOVA (multiple groups) followed by post hoc Bonferroni test. The criterion for statistical significance was $P<0.05$.

REFERENCES

1. Serhan C N, Savill J. Resolution of inflammation: the beginning programs the end. *Nat Immunol* 2005, 6(12): 1191-1197.
2. Serhan C N. A search for endogenous mechanisms of anti-inflammation uncovers novel chemical mediators: missing links to resolution. *Histochem Cell Biol* 2004, 122(4): 305-321.
3. Tabas I, Glass C K. Anti-inflammatory therapy in chronic disease: challenges and opportunities. *Science* 2013, 339 (6116): 166-172.
4. Buckley C D, Gilroy D W, Serhan C N, Stockinger B, Tak P P. The resolution of inflammation. *Nat Rev Immunol* 2013, 13(1): 59-66.
5. Samuelsson B. Role of basic science in the development of new medicines: examples from the eicosanoid field. *J Biol Chem* 2012, 287(13): 10070-10080.
6. Shimizu T. Lipid mediators in health and disease: enzymes and receptors as therapeutic targets for the regulation of immunity and inflammation. *Annu Rev Pharmacol Toxicol* 2009, 49: 123-150.
7. Chiang N, Fredman G, Backhed F, Oh S F, Vickery T, Schmidt B A, et al. Infection regulates pro-resolving mediators that lower antibiotic requirements. *Nature* 2012, 484(7395): 524-528.
8. Flower R J, Vane J R. Inhibition of prostaglandin biosynthesis. *Biochem Pharmacol* 1974, 23(10): 1439-1450.
9. Kasuga K, Yang R, Porter T F, Agrawal N, Petasis N A, Irimia D, et al. Rapid appearance of resolvin precursors in inflammatory exudates: novel mechanisms in resolution. *J Immunol* 2008, 181(12): 8677-8687.
10. Calder P C. Fatty acids and inflammation: the cutting edge between food and pharma. *Eur J Pharmacol* 2011, 668 Suppl 1: S50-58.
11. Rapoport S I. Translational studies on regulation of brain docosahexaenoic acid (DHA) metabolism in vivo. *Prostaglandins Leukot Essent Fatty Acids* 2013, 88(1): 79-85.
12. De Caterina R. n-3 fatty acids in cardiovascular disease. *N Engl J Med* 2011, 364(25): 2439-2450.
13. Colgan S P, Ehrentraut S F, Glover L E, Kominsky D J, Campbell E L. Contributions of neutrophils to resolution of mucosal inflammation. *Immunol Res* 2013, 55(1-3): 75-82.
14. Serhan C N, Clish C B, Brannon J, Colgan S P, Chiang N, Gronert K. Novel functional sets of lipid-derived mediators with antiinflammatory actions generated from omega-3 fatty acids via cyclooxygenase 2-nonsteroidal antiinflammatory drugs and transcellular processing. *J Exp Med* 2000, 192(8): 1197-1204.
15. Serhan C N, Hong S, Gronert K, Colgan S P, Devchand P R, Mirick G, et al. Resolvins: a family of bioactive products of omega-3 fatty acid transformation circuits initiated by aspirin treatment that counter proinflammation signals. *J Exp Med* 2002, 196(8): 1025-1037.
16. Serhan C N, Dalli J, Karamnov S, Choi A, Park C K, Xu Z Z, et al. Macrophage proresolving mediator maresin 1 stimulates tissue regeneration and controls pain. *FASEB J* 2012, 26(4): 1755-1765.
17. Dalli J, Serhan C N. Specific lipid mediator signatures of human phagocytes: microparticles stimulate macrophage efferocytosis and pro-resolving mediators. *Blood* 2012, 120(15): e60-72.
18. Zhang M J, Spite M. Resolvins: anti-inflammatory and proresolving mediators derived from omega-3 polyunsaturated fatty acids. *Annu Rev Nutr* 2012, 32: 203-227.
19. Giera M, Ioan-Facsinay A, Toes R, Gao F, Dalli J, Deelder A M, et al. Lipid and lipid mediator profiling of human synovial fluid in rheumatoid arthritis patients by means of LC-MS/MS. *Biochim Biophys Acta* 2012, 1821 (11): 1415-1424.
20. Mas E, Croft K D, Zahra P, Barden A, Mori T A. Resolvins D1, D2, and Other Mediators of Self-Limited Resolution of Inflammation in Human Blood following n-3 Fatty Acid Supplementation. *Clin Chem* 2012, 58(10): 1476-1484.
21. Lemaitre R N, Tanaka T, Tang W, Manichaikul A, Foy M, Kabagambe E K, et al. Genetic loci associated with plasma phospholipid n-3 fatty acids: a meta-analysis of genome-wide association studies from the CHARGE Consortium. *PLoS Genet* 2011, 7(7): e1002193.
22. Crawford M A, Leigh Broadhurst C, Guest M, Nagar A, Wang Y, Ghebremeskel K, et al. A quantum theory for the irreplaceable role of docosahexaenoic acid in neural cell signalling throughout evolution. *Prostaglandins Leukot Essent Fatty Acids* 2013, 88(1): 5-13.
23. Hussein N, Fedorova I, Moriguchi T, Hamazaki K, Kim H Y, Hoshiba J, et al. Artificial rearing of infant mice leads to n-3 fatty acid deficiency in cardiac, neural and peripheral tissues. *Lipids* 2009, 44(8): 685-702.
24. van Gils J M, Zwaginga J J, Hordijk P L. Molecular and functional interactions among monocytes, platelets, and endothelial cells and their relevance for cardiovascular diseases. *J Leukoc Biol* 2009, 85(2): 195-204.
25. Bannenberg G L, Chiang N, Ariel A, Arita M, Tjonahen E, Gotlinger K H, et al. Molecular circuits of resolution: formation and actions of resolvins and protectins. *J Immunol* 2005, 174(7): 4345-4355.
26. Granger D N, Kubes P. The microcirculation and inflammation: modulation of leukocyte-endothelial cell adhesion. *J Leukoc Biol* 1994, 55(5): 662-675.
27. Spite M, Norling L V, Summers L, Yang R, Cooper D, Petasis N A, et al. Resolvin D2 is a potent regulator of leukocytes and controls microbial sepsis. *Nature* 2009, 461(7268): 1287-1291.
28. Luscinskas F W, Cybulsky M I, Kiely J M, Peckins C S, Davis V M, Gimbrone M A, Jr. Cytokine-activated human endothelial monolayers support enhanced neutrophil transmigration via a mechanism involving both endothelial-leukocyte adhesion molecule-1 and intercellular adhesion molecule-1. *J Immunol* 1991, 146(5): 1617-1625.
29. Sun Q, Ma J, Campos H, Rexrode K M, Albert C M, Mozaffarian D, et al. Blood concentrations of individual long-chain n-3 fatty acids and risk of nonfatal myocardial infarction. *Am J Clin Nutr* 2008, 88(1): 216-223.
30. Khaw K T, Friesen M D, Riboli E, Luben R, Wareham N. Plasma phospholipid fatty acid concentration and incident coronary heart disease in men and women: the EPIC-Norfolk prospective study. *PLoS Med* 2012, 9(7): e1001255.
31. Oda E, Hatada K, Katoh K, Kodama M, Nakamura Y, Aizawa Y. A case-control pilot study on n-3 polyunsaturated fatty acid as a negative risk factor for myocardial infarction. *Int Heart J* 2005, 46(4): 583-591.
32. Rissanen T, Voutilainen S, Nyyssonen K, Lakka T A, Salonen J T. Fish oil-derived fatty acids, docosahexaenoic acid and docosapentaenoic acid, and the risk of acute coronary events: the Kuopio ischaemic heart disease risk factor study. *Circulation* 2000, 102(22): 2677-2679.

33. Qiu F H, Wada K, Stahl G L, Serhan C N. IMP and AMP deaminase in reperfusion injury down-regulates neutrophil recruitment. *Proc Natl Acad Sci USA* 2000, 97(8): 4267-4272.
34. Serhan C N, Petasis N A. Resolvins and protectins in inflammation resolution. *Chem Rev* 2011, 111(10): 5922-5943.
35. Serhan C N, Yang R, Martinod K, Kasuga K, Pillai P S, Porter T F, et al. Maresins: novel macrophage mediators with potent antiinflammatory and proresolving actions. *J Exp Med* 2009, 206(1): 15-23.
36. Furman M I, Dauerman H L, Goldberg R J, Yarzebski J, Lessard D, Gore J M. Twenty-two year (1975 to 1997) trends in the incidence, in-hospital and long-term case fatality rates from initial Q-wave and non-Q-wave myocardial infarction: a multi-hospital, community-wide perspective. *J Am Coll Cardiol* 2001, 37(6): 1571-1580.
37. Spite M, Serhan C N. Novel lipid mediators promote resolution of acute inflammation: impact of aspirin and statins. *Circ Res* 2010, 107(10): 1170-1184.
38. Dangi B, Obeng M, Nauroth J M, Chung G, Bailey-Hall E, Hallenbeck T, et al. Metabolism and biological production of resolvins derived from docosapentaenoic acid (DPAn-6). *Biochem Pharmacol* 2010, 79(2): 251-260.
39. Chiu C Y, Gomolka B, Dierkes C, Huang N R, Schroeder M, Purschke M, et al. Omega-6 docosapentaenoic acid-derived resolvins and 17-hydroxydocosahexaenoic acid modulate macrophage function and alleviate experimental colitis. *Inflamm Res* 2012, 61(9): 967-976.
40. Barrett E, Fitzgerald P, Dinan T G, Cryan J F, Ross R P, Quigley E M, et al. *Bifidobacterium breve* with alpha-Linolenic Acid and Linoleic Acid Alters Fatty Acid Metabolism in the Maternal Separation Model of Irritable Bowel Syndrome. *PLoS One* 2012, 7(11): e48159.
41. Yang R, Chiang N, Oh S F, Serhan C N. Metabolomics-lipidomics of eicosanoids and docosanoids generated by phagocytes. *Curr Protoc Immunol* 2011, Chapter 14: Unit 14 26.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound having the formulae:

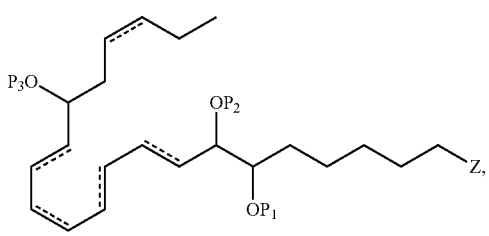
(I)

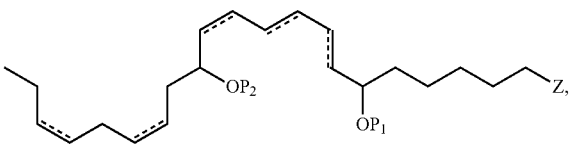
(III)

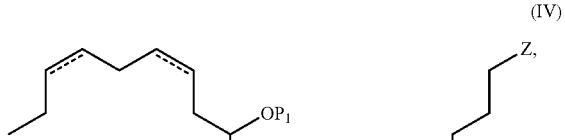
(IV)

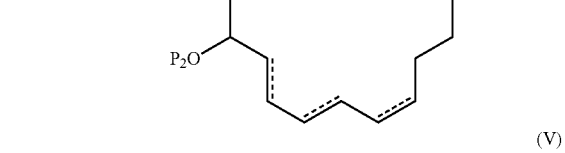
(V)

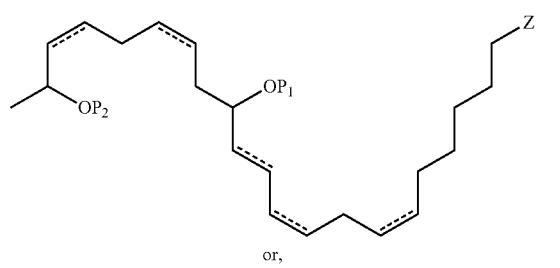
or,

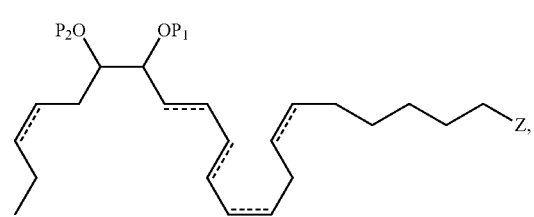
(XI)

wherein each of $P_1$, $P_2$ and/or $P_3$ when present, individually is a protecting group or a hydrogen atom;

----- when present, represents a double bond; and wherein Z is COOH and $P_1$, $P_2$ and/or $P_3$ when present are not all hydrogen atoms.

2. The compound of claim 1, wherein the compound has the formulae:

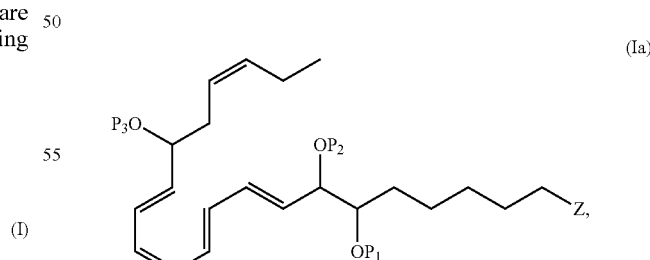
(Ia)

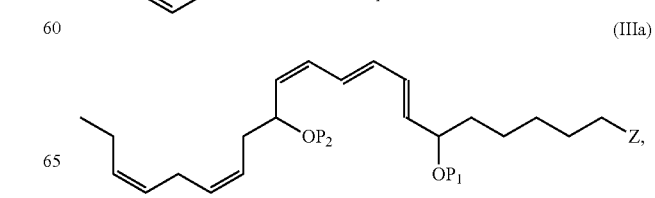
(IIIa)

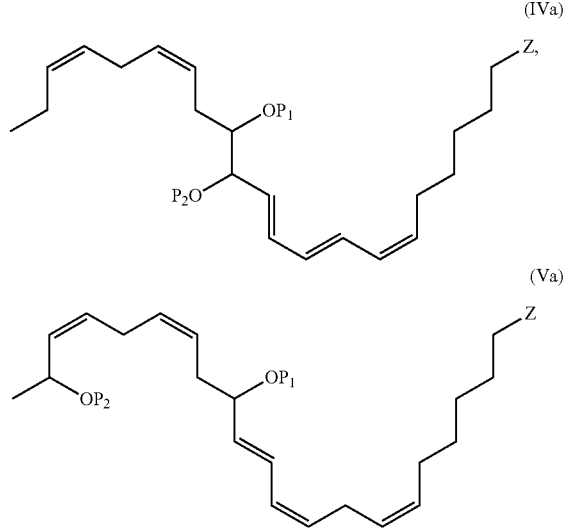
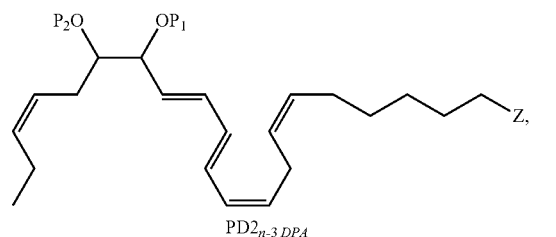
wherein $P_1$, $P_2$ and/or $P_3$, when present, individually are hydrogen atoms or a protecting group; and
wherein Z is COOH and $P_1$, $P_2$ and/or, $P_3$ when present are not all hydrogen atoms.
* * * * *